(12) United States Patent
Kerr et al.

(10) Patent No.: US 8,622,252 B2
(45) Date of Patent: Jan. 7, 2014

(54) PERSONAL CARE COMPOSITION FOAMING PRODUCT AND FOAMING DISPENSER

(75) Inventors: George Scott Kerr, Mason, OH (US); Robert Drennan Lewis, West Chester, OH (US); Mark Thomas Lund, Mason, OH (US); Dimitris Ioannis Collias, Mason, OH (US); Christopher Gerald Donner, Libery Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/972,147

(22) Filed: Dec. 17, 2010

(65) Prior Publication Data

US 2011/0284586 A1    Nov. 24, 2011

Related U.S. Application Data

(60) Provisional application No. 61/287,923, filed on Dec. 18, 2009, provisional application No. 61/333,954, filed on May 12, 2010.

(51) Int. Cl.
*B67D 7/76* (2010.01)

(52) U.S. Cl.
USPC ........................ 222/190; 222/321.9

(58) Field of Classification Search
USPC ........ 222/190, 321.1, 321.7, 321.9, 340, 341, 222/145.5, 145.6
See application file for complete search history.

(56) References Cited

U.S. PATENT DOCUMENTS

| | | | |
|---|---|---|---|
| 3,578,387 A | 5/1971 | Charles | |
| 3,709,437 A | 1/1973 | Wright | |
| 3,937,364 A | 2/1976 | Wright | |
| 3,977,826 A | 8/1976 | Iscowitz | |
| 4,022,351 A | 5/1977 | Wright | |
| 4,147,306 A | 4/1979 | Bennett | |
| 4,184,615 A | 1/1980 | Wright | |
| 4,615,467 A | 10/1986 | Grogan | |
| 4,796,812 A | 1/1989 | Grollier | |
| 4,921,170 A | 5/1990 | Grollier | |
| 5,344,761 A | 9/1994 | Citri | |
| 5,443,569 A | 8/1995 | Uehira | |
| 5,813,576 A * | 9/1998 | Iizuka et al. | 222/190 |
| 6,106,578 A | 8/2000 | Jones | |
| 6,446,840 B2 * | 9/2002 | Ophardt et al. | 222/190 |
| 6,536,629 B2 * | 3/2003 | van der Heijden | 222/190 |
| 6,604,693 B2 * | 8/2003 | Santagiuliana | 239/343 |
| 6,835,210 B1 | 12/2004 | Bartolone | |

(Continued)

FOREIGN PATENT DOCUMENTS

| | | |
|---|---|---|
| EP | 1 142 563 A1 | 10/2001 |
| FR | 2604622 | 12/1990 |

(Continued)

OTHER PUBLICATIONS

Leung, A Y, "Encyclopedia of Common Natural Ingredients Used in Food, Drugs and Cosmetics (2d Edition)", Jan. 1, 1996, Wiley, NY, US, p. 446.

*Primary Examiner* — Lien Ngo
(74) *Attorney, Agent, or Firm* — Carl J. Roof

(57) ABSTRACT

A manually-actuable, non-aerosol dispenser to be used with a personal care composition having a relatively higher viscosity that gives a desired foamed composition generated from a manually-actuable, non-aerosol dispenser.

21 Claims, 6 Drawing Sheets

(56) References Cited

U.S. PATENT DOCUMENTS

| | | | |
|---|---|---|---|
| 7,040,507 B2 | 5/2006 | Koike | |
| 7,641,077 B2 * | 1/2010 | Law et al. | 222/190 |
| 7,850,049 B2 | 12/2010 | Ciavarella | |
| 7,955,400 B2 | 6/2011 | Fujinuma | |
| 8,025,702 B2 | 9/2011 | Fujinuma | |
| 8,025,703 B2 | 9/2011 | Ogawa | |
| 8,056,767 B2 * | 11/2011 | Mizushima et al. | 222/190 |
| 2002/0058017 A1 | 5/2002 | Tajima | |
| 2003/0180238 A1 | 9/2003 | Sakurai | |
| 2003/0192133 A1 | 10/2003 | Matsuo | |
| 2004/0213752 A1 | 10/2004 | Fujinuma | |
| 2004/0254253 A1 * | 12/2004 | Culeron et al. | 516/115 |
| 2005/0222001 A1 | 10/2005 | Baumeister | |
| 2005/0226824 A1 * | 10/2005 | Kawa et al. | 424/59 |
| 2006/0054634 A1 | 3/2006 | Mekata | |
| 2006/0207037 A1 | 9/2006 | Fadel | |
| 2006/0219738 A1 | 10/2006 | Ilzuka | |
| 2008/0087293 A1 | 4/2008 | Glenn | |
| 2010/0126522 A1 | 5/2010 | Fujinuma | |
| 2010/0126523 A1 | 5/2010 | Fujinuma | |
| 2010/0236570 A1 | 9/2010 | Fujinuma | |
| 2010/0242187 A1 | 9/2010 | Miyabe | |
| 2010/0251488 A1 | 10/2010 | Fujinuma | |
| 2010/0257677 A1 | 10/2010 | Miyabe | |
| 2010/0299848 A1 | 12/2010 | Fujinuma | |
| 2010/0313905 A1 | 12/2010 | Fujinuma | |
| 2010/0316583 A1 | 12/2010 | Fujinuma | |
| 2011/0073128 A1 | 3/2011 | Ogawa | |
| 2011/0214682 A1 | 9/2011 | Fujinuma | |
| 2011/0284421 A1 | 11/2011 | Lane | |
| 2011/0284584 A1 | 11/2011 | Velazquez | |
| 2011/0284587 A1 | 11/2011 | Galazka | |

FOREIGN PATENT DOCUMENTS

| | | | |
|---|---|---|---|
| JP | 7033860 U | 6/1995 | |
| JP | 08230919 A | 9/1996 | |
| JP | 10128189 A | 5/1998 | |
| JP | 2007145726 A | 6/2007 | |
| JP | 2007261688 A | 10/2007 | |
| JP | 2007-291015 A | 11/2007 | |
| JP | 2007-291016 A | 11/2007 | |
| JP | 2007-314523 A | 12/2007 | |
| JP | 2007-314524 A | 12/2007 | |
| JP | 2008188485 A | 8/2008 | |
| JP | 2009-149322 A | 7/2009 | |
| JP | 2009-149323 A | 7/2009 | |
| JP | 2009-149324 A | 7/2009 | |
| JP | 2009-149325 A | 7/2009 | |
| JP | 2009-149326 A | 7/2009 | |
| JP | 2009-149327 A | 7/2009 | |
| JP | 2010-006804 A | 1/2010 | |
| JP | 2010-006805 A | 1/2010 | |
| WO | WO 91/14759 | 10/1991 | |
| WO | WO 97/013585 | 4/1997 | |
| WO | WO2004078901 A1 | 9/2004 | |
| WO | WO 2009/130461 | 10/2009 | |
| WO | WO 2010/106789 | 9/2010 | |

* cited by examiner

PERSONAL CARE COMPOSITION FOAMING PRODUCT AND FOAMING DISPENSER

CROSS REFERENCE TO RELATED APPLICATIONS

This application claims the benefit of U.S. Provisional Application Ser. No. 61/287,923 filed Dec. 18, 2009 and U.S. Provisional Application Ser. No. 61/333,954 filed May 12, 2010.

FIELD OF THE INVENTION

The present invention relates to a higher viscosity personal care composition for use in combination with a foaming dispenser such that a desired foam profile is produced.

BACKGROUND OF THE INVENTION

Desired foam characteristics for consumer products, such as personal care compositions, are dependent upon the end use and consumer expectations. If a consumer foamed product is expected to be applied to a surface other than the hands of the consumer, there are properties that define acceptable foam characteristics. Acceptable foam characteristics in personal care composition are exemplified by foam that holds its shape and stays in a consistent form in order to transfer from a consumer's hand to the desired location on the consumer's body (e.g., hair, face, arms, legs, etc.). If foam collapses prematurely and becomes a liquid, any movement of the consumer's hand, specifically the palm of the hand, from a horizontal position to a non-horizontal position for application causes the foam to run, drip or otherwise move from the consumer's hand before the foam reaches the desired location and is considered undesirable. This foam characteristic is especially undesirable when working with personal care compositions that can change the color or tint the surface it touches, such as hair dying composition or skin lightening or tinting compositions.

Likewise, foam that is too "airy" cause consumers to apply the personal care composition at a higher frequency as the amount of personal care composition per dosage is diminished with a foam containing more air than composition.

Manually-actuable, non-aerosol dispenser useful herein includes squeeze foamers. The basic mechanism by which such foamers operate is that liquid from a container reservoir is pumped into a liquid/air mixing chamber where air is mixed with liquid held within the container. Foam is generated (air into liquid) and then passed through one or more screens to refine the foam which is then dispensed. Traditionally, liquids that were used in such foamers were described as having a "high" viscosity when the viscosity (at 25° C.) is 100 cps (0.1 pascal seconds) or less. See US 2004/0254253 A1. Although viscosities (at 25° C.) of up to 300 cps (0.3 pascal seconds) of liquids for such foamers has been discussed. See US 2004/0213752 A1. Use of polymers to increase the viscosity of a personal cleaning composition that is foamed is known, but with target viscosities of the composition are targeted to be less than 100 cps (0.1 pascal seconds). See WO 91/14759.

One drawback of the manner under which the manually-actuable, non-aerosol dispenser foamers operate to generate foam is that higher viscosity materials (higher than 300 cps or 0.3 pascal seconds) make squeezing too difficult as large amounts of work (an applied force moving an object in a distance) is required to expel higher viscosity liquids from such foaming containers.

Additional benefits of the present invention include a desired foam specific volume of the resulting foamed personal care composition, reduction in force required to actuate the manually-actuable, non-aerosol dispenser, improved end results of the personal care composition such as improved color results and improved amount of personal care product delivered per dosage. The present disclosure includes foamers that reduce the amount of work required to expel a desired quantity of foam, while substantially preserving the desired foam specific volume, thereby improving the ease of dispensing foam personal care compositions.

SUMMARY OF THE INVENTION

A personal care article comprising (1) a personal care composition comprising a low-shear viscosity of at least 100 cps; the personal care composition being shear-thinning; (2) a manually-actuable, non-aerosol dispensers comprising: (a) a reservoir for holding a liquid to be dispensed in the form of foam; the reservoir comprises a volume such that the reservoir volume is larger than the volume of the personal care composition contained within the reservoir; the reservoir further comprising a headspace, the headspace comprising air; (b) a foamer assembly which can be mounted on or in an opening of the reservoir; the foamer assembly comprises a dip tube, a mixing chamber and a dispensing head; the dip tube extends into the reservoir and into contact with the personal care composition, the dip tube fluidly connecting the mixing chamber with the personal care composition, the mixing chamber fluidly connected to a dispensing head, the dispensing head comprising a foam fluid connection contained within the dispensing head and the dispensing head further comprising a dispensing orifice; the foam fluid connection containing one or more porous elements; the mixing chamber comprises an outer wall which defines an internal volume of the mixing chamber; the outer wall comprises a top edge comprising a circumference; the circumference defining a top area; the mixing chamber further comprising at least one air ingress orifice, at least one liquid ingress orifice and at least one mixing chamber egress orifice;

wherein the at least one air ingress orifice and at least one liquid ingress orifice are selected such that a ratio of personal care composition to air is from about 1:6 to about 1:15, preferably from about 1:8 to about 1:12, preferably 1:10; or wherein the mixing chamber egress orifice area is selected to be smaller than the area of the circumference of the top edge of the outer wall of the mixing chamber; or wherein the at least one air ingress orifice and at least one liquid ingress orifice are selected such that the manually-actuable, non-aerosol dispensers has a foam output of about 0.5 g/stroke to about 5.0 g/stroke with a foam specific volume of about 6 mug to about 14 ml/g.

BRIEF DESCRIPTION OF THE DRAWINGS

FIG. 1A is a magnified view, taken along lines 1A-1A of FIG. 1, of a mesh disposed near a diffuser opening or mixing chamber egress orifice of the dispenser;

FIG. 1B is a magnified view, taken along lines 1B-1B of FIG. 1, of a mesh, disposed near a dispenser head orifice;

FIG. 3A is a magnified view, taken along lines 3A-3A of FIG. 3, of a mesh disposed near a diffuser opening or mixing chamber egress orifice of the dispenser;

FIG. 3B is a magnified view, taken along lines 3B-3B of FIG. 3, of a mesh, disposed near a dispenser head orifice.

DETAILED DESCRIPTION OF THE INVENTION

Figure 1:
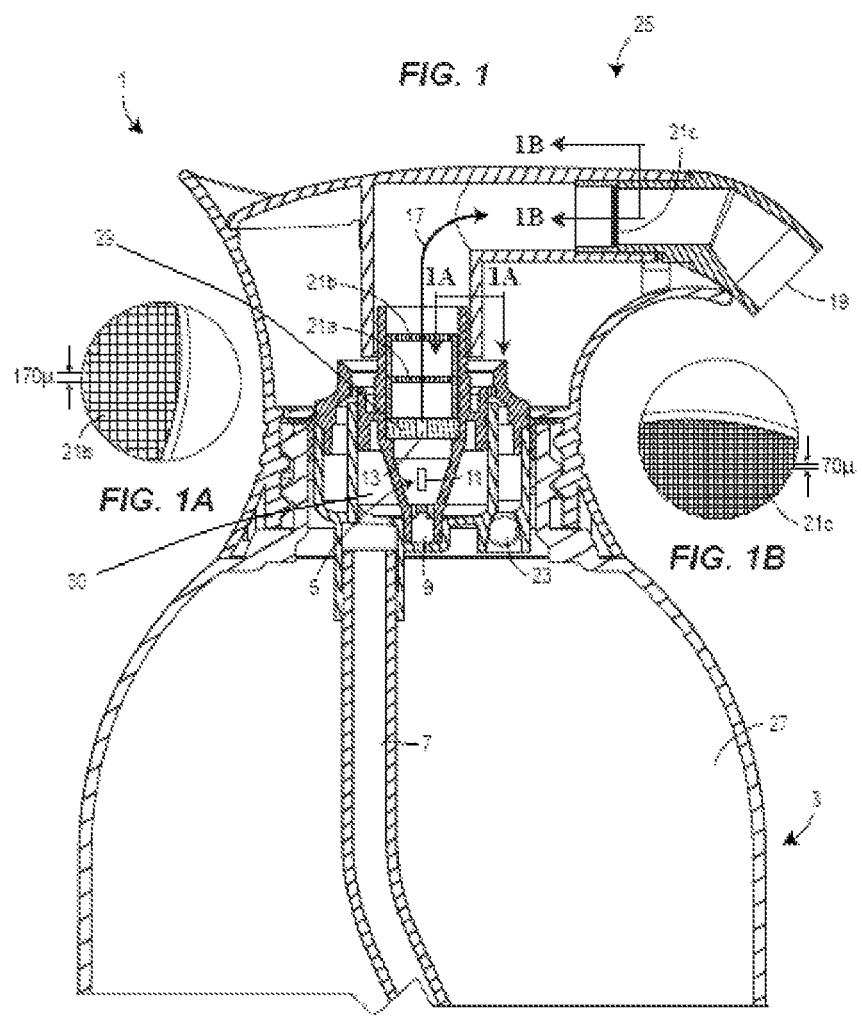
FIG. 1 illustrates an embodiment of the manually-actuable, non-aerosol dispenser cross sectional view.
Figure 2:
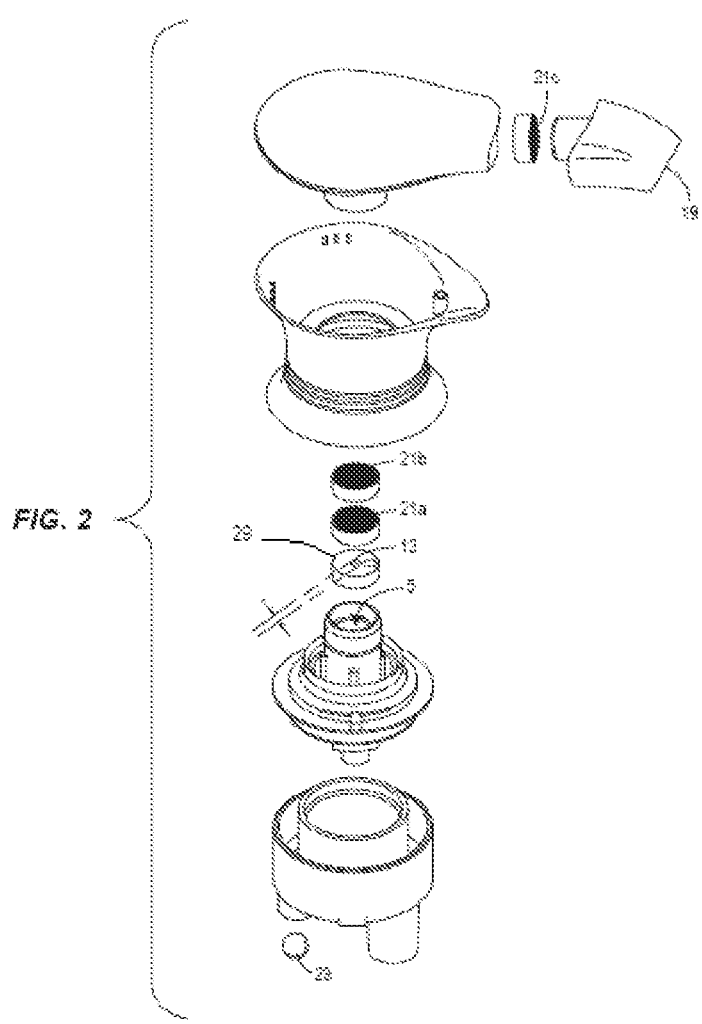
FIG. 2 is an exploded view of a dispenser head of the dispenser of FIG. 1.

The personal care article of the present application utilizes a personal care composition comprising certain rheological characteristics, such as having a desired low-shear viscosity and that the composition is shear-thinning (e.g. comprising a viscosity which decreases as shear is applied to the composition) during dispensing of the personal care composition.

The desired viscosity profile ensures a desired consumer experience when in contact with the personal care composition. The foam specific volume is impacted by the rheological properties and the liquid to air ratio. The rheology properties of the composition after it is foamed, and the foam collapsed, is selected such that the composition does not drip or run from the surface on which it is applied, such as hair.

As used herein "foam" means a personal care composition which after being passed through a manually-actuable, non-aerosol dispenser has bubbles that sustain their shape and give a volume independent of any type of container. It is preferably that the volume is a foam specific volume from about 6 ml/g to about 14 ml/g, such as about 7.5 ml/g to about 12 ml/g, such as from about 8 ml/g to about 11 ml/g. One embodiment is a foam specific volume of about 10 ml/g.

As used herein "stroke" means deflecting a reservoir that is placed against a vertical flat surface, such as a wall, on the side of the reservoir opposite the wall, 30 mm towards the wall at a rate of 20 mm per second. "Squeeze" or "dispensed" are also included in the term "stroke".

A manually-actuable, non-aerosol dispenser is optionally designed to have a foam output per stroke or squeeze from about 0.5 gram/stroke to about 5.0 gram/stroke, preferably about 0.8 gram/stroke to about 4.0 gram/stroke, preferably from about 1.0 gram/stroke to about 4.0 gram/stroke. In one embodiment, the manually-actuable, non-aerosol dispenser is optionally designed to have a foam output per stroke or squeeze from about 1.8 gram/stroke to about 2.2 gram/stroke.

A manually-actuable, non-aerosol dispenser is optionally designed to have a foam output per stroke or squeeze from about 3 ml/stroke to about 70 ml/stoke, preferably from about 76 ml/stroke to about 48 ml/stroke, preferably from about 8 ml/stroke to about 44 ml/stroke, preferably from about 18 ml/stroke to about 22 ml/stroke.

Applicants have found that the range of foam specific volume above gives a desired experience by consumers, with the foamed personal care composition being neither too wet (resulting in running or dripping) or too dry (low amounts of product deposited). The foam specific volume will somewhat be controlled by the amount of force applied from squeeze to squeeze by the consumer and it is anticipated that foam output and foam specific volume will vary from consumer to consumer.

Manually-actuable, non-aerosol dispensers for foam generation are well known in the art. These foam dispensers comprise a reservoir for holding a liquid to be dispensed in the form of foam with an assembly which can be mounted on or in an opening of the reservoir. The assembly comprises a dip tube which extends into the reservoir and into contact with the personal care composition, then the dip tube extends in the opposite direction from the reservoir into a mixing chamber, a liquid pump for pumping the liquid from the reservoir and an air pump to mix air with the liquid in the mixing chamber in order to form foam. The foam is dispensed out of the mixing chamber and through a dispensing channel out of a dispensing head comprising a dispensing orifice. In the dispensing channel one or more porous elements such as sieves or screens that may be arranged to form homogeneous foam.

The amount of work required for dispensing the personal care composition with the higher viscosities described herein (higher than 300 cps (0.3 pascal seconds)) is unique verses known lower viscosity personal care compositions such as foam hand wash products. It is unique in that with lower viscosity personal care composition, more work is expended moving air than the liquid in such systems. For higher viscosity personal care compositions (higher than 300 cps (0.3 pascal seconds)), more work is expended to move the liquid than the air in such systems.

The use of higher viscosity personal care compositions and the amount of work required to move the higher viscosity personal care composition further poses unique problems relating the amount of shear generated in the manually-actuable, non-aerosol dispensers suitable for use herein. The use of higher viscosity personal care compositions further affects the ratio of liquid to air. The ratio of liquid (personal care composition) to air is from about 1:6 to about 1:15, preferably from about 1:8 to about 1:12, preferably 1:10.

The amount of work, shear generation, residence time of liquid in the shear and liquid to air ratio are aspects that can be attributed to the manually-actuable, non-aerosol dispenser structure. The portions of the manually-actuable, non-aerosol dispenser structure that have been found to affect the amount of work to dispense the manually-actuable, non-aerosol dispenser include the dimensions of the dip tube, dimensions of the air ingress into the mixing chamber, mixing chamber dimensions, including the ingress and egress orifices from the mixing chamber, dispensing channel dimensions, porous elements (such as screens or meshes) and dispensing head orifice.

The manually-actuable, non-aerosol dispenser comprises a reservoir. The reservoir comprises a volume such that the reservoir volume is larger than the volume of the personal care composition contained within the reservoir. The area of the reservoir that is not occupied by the personal care composition is the head space. The head space should remain relatively free of the personal care composition or bubbles of the personal care composition. If the reservoir is shaken or inverted while the personal care composition is contained therein, the head space should remain relatively free of the personal care composition or bubbles thereof. As used in this paragraph, "relatively free" means less than 50%, such as less than 75%, such as less than 90%, such as 75% to 100% of the head space volume is free from the personal care composition or bubbles thereof.

The reservoir is selected to have enough volume to contain the personal care composition, any part of the mechanism for foaming the personal care composition (such as a dip tube) and still have head space. The reservoir volume in one embodiment is selected to be from about 100 ml to about 500 ml, from about 150 ml to about 400 ml, such as 250 ml. The ratio of the reservoir volume to personal care composition volume is from about 0.30 to about 0.70, such as from about 0.40 to about 0.55.

The shape of the reservoir may be selected such that when the personal care composition is contained within the reservoir, the force required per volume displacement may be optimized. In one embodiment, the force required per volume displacement is optimized when the shape of the bottle is selected to have an elliptical cross-section as viewed from vertical axis of the bottle (from the top or bottom of the bottle). The elliptical cross-section is preferably concentric such that a neck suitable for a threaded or snap-on cap may be used to close the reservoir. The major axis of the elliptical cross-section is orientated such that it is perpendicular to the force applied to the reservoir surface FIG. 1 illustrates a general structure for a personal care composition product (25) comprising a foamer assembly (1) and a reservoir (3).

The reservoir (3) having a reservoir volume (27) that contains the personal care composition is fluidly connected to the mixing chamber (5) such that the personal care composition is transported from the reservoir (3) when the manually-actuable, non-aerosol dispenser (25) is dispensed (e.g., "stroke"). The fluid connection is a dip tube (7). The dip tube (7) diameter for the present personal care composition having a relatively higher viscosity requires a relatively larger diameter in order to allow for easy dispensing (low amount of force needed to dispense) and to achieve the desired foam specific volume.

The dip tube (7) diameter is preferably selected to have a diameter of greater than 2.0 mm, preferably from about 2.0 mm to about 5.0 mm, more preferably from about 2.5 mm to about 4.0 mm. The viscosity of the liquid with a dip tube (7) diameter between about 2.0 mm and about 4.0 mm allows for the liquid to be conveyed from the reservoir (3) into the mixing chamber (5) with lower amounts of force by the user during dispensing (e.g., "stroke") while achieving the desired foam density discussed herein.

The mixing chamber (5) comprises at least one air ingress orifice (9), at least one liquid ingress orifice (11) and at least one mixing chamber egress orifice (13). The mixing chamber (5) further comprises an internal volume and an exterior wall, which defines the internal volume of the mixing chamber (5). The mixing chamber (5) allows for the combination of the personal care composition and air to begin the formation of the foamed personal care composition. Modification of the various orifice (9, 11, 13) areas (the two-dimensions of the indicating orifices that comprise part of the mixing chamber (5) exterior wall) can affect the foam specific density, particularly the correlation of the air ingress orifice (9) and the liquid ingress orifice (11) such that the liquid to air ratio is appropriate.

The air ingress orifice (9) is suitable to convey air that has entered into the headspace of the reservoir (3). The mixing chamber (5) may comprise more than one air ingress orifice (9). In one embodiment, the mixing chamber (5) comprises one air ingress orifice (9). The area of the air ingress orifice (9) may be from about 0.62 mm$^2$ (about a 0.2 mm diameter circular air ingress orifice) to about 3.14 mm$^2$ (about a 1 mm diameter circular air ingress orifice), preferably from about 1.26 mm$^2$ (about a 0.4 mm diameter circular air ingress orifice) to about 1.88 mm$^2$ (about a 0.8 mm diameter circular air ingress orifice). If more than one air ingress orifice (9) is selected, the total area of all air ingress orifices (9) should be used. Communication of the air in to the mixing chamber (5) via the air ingress orifice (9) can be and indirect communication with the mixing chamber (5) or a direct communication with the mixing chamber (5).

Similarly, the liquid ingress orifice (11) is suitable to fluidly convey the personal care composition into the mixing chamber (5) from the reservoir (3), preferably via a dip tube (7). In one embodiment, the mixing chamber (5) comprises more than one liquid ingress orifice (11). In one embodiment, the mixing chamber (5) comprises three liquid ingress orifices (11). The area of the liquid ingress orifice (11) should be from about 1.5 mm$^2$ to about 3 mm$^2$. In one embodiment the liquid ingress orifice (11) should be from about 1.8 mm$^2$ to about 2.3 mm$^2$. If more than one liquid ingress orifice (9) is selected, the total area of all air ingress orifices (9) should be used. For example, a total area of 2.0 mm$^2$ for three liquid ingress orifices (11) would equate the total areas of all three liquid ingress orifices (11) combined. The fluid conveyance from the reservoir (3) to the mixing chamber (5) may be an indirect communication pathway with the mixing chamber (5) or a direct communication pathway with the mixing chamber (5).

As used herein "indirect communication" means that the conveyance of the air or personal care composition to the mixing chamber (5) travels along a pathway through some other physical structure before entering into the mixing chamber (5). For example, the air or personal care composition will come into contact with the exterior wall of the mixing chamber (5) before entering into the mixing chamber (5) through the respective orifice (9, 11). In one embodiment, a void volume (30) is contiguous with the exterior wall of the mixing chamber (5). The air or the personal care composition is conveyed from the reservoir, through the dip tube (7) into the void volume (30) external to the mixing chamber (5). The void volume (30) is in air and/or in liquid communication with the air ingress orifice (9) and/or the liquid ingress orifice (11), respectively.

As used herein "direct communication" means that the conveyance of the air or personal care composition to the mixing chamber (5) travels directly into the mixing chamber (5). For example, the air or personal care composition will come into contact with the internal volume of the mixing chamber (5) through the respective orifice (9, 11) without contacting a component exterior to the mixing chamber (5).

In one embodiment, the mixing chamber egress orifice (13) is selected to create an increase in pressure within the mixing chamber (5). The mixing chamber (5) may comprise more than one mixing chamber orifice (13). In one embodiment, the mixing chamber (5) comprises one mixing chamber egress orifice (13).

The mixing chamber (5) has an outer wall creating an internal volume of the mixing chamber (5). The top edge of the outer wall defines a circumference. The mixing chamber egress orifice (13) may be the same size area of the circumference of the mixing chamber (5) top edge, but preferably is selected to be smaller area than the area of the circumference of the mixing chamber (5) top edge so as to create an increase in pressure in the mixing chamber (5). The area of the mixing chamber egress orifice (13) may be between about 0.314 mm$^2$ (0.1 mm diameter circular orifice) to about 9.42 mm$^2$ (3 mm diameter circular orifice). In one embodiment, the mixing chamber egress orifice (13) comprises an area of about 2.512 mm$^2$ (0.8 mm diameter circular orifice) to about 5.652 mm$^2$ (1.8 mm diameter circular orifice). If more than one mixing chamber egress orifice (13) is present, the total area of all of the mixing chamber egress orifices should be considered.

In an embodiment, a diffuser plate (29) comprises the mixing chamber egress orifice (13). The diffuser plate (29)

may be part of the mixing chamber (5) structure or it may be a separate component that fits into the mixing chamber (5).

The mixing chamber (5) is fluidly connected to the foamer assembly (1). The personal care composition enters into the mixing chamber (5) via the liquid ingress orifice (11) and mixes with air which enters the mixing chamber (5) via the air ingress orifice (9). It is believed that the diffuser plate (29) helps increase the residence time of the personal care composition in the mixing chamber (5). As the residence time of the personal care composition increases in the mixing chamber (5), the personal care composition is subjected to more shear and generates bubbles.

The air is ordinarily supplied from the environment exterior to the manually-actuable, non-aerosol dispenser (25), the air entering the manually-actuable, non-aerosol dispenser (25) after a stroke which is then located in the headspace of the reservoir (3). The controlled entry or exit of air into the manually-actuable, non-aerosol dispenser (25) reservoir (3) headspace may be accomplished by a ball valve (23) or silicone seal or gasket. The ball valve or silicone seal or gasket may be located in the foamer assembly (1) an in communication with the headspace. In one embodiment, the ball valve (23, silicone seal or gasket is located to communicate between the reservoir (3) and the air external to the manually-actuable, non-aerosol dispenser (25) such that when the manually-actuable, non-aerosol dispenser (25) is being dispensed, the ball valve (23) silicone seal or gasket excludes entry of air external to the manually-actuable, non-aerosol dispenser (25) into the reservoir (3) headspace so that the air in the headspace is conveyed to the mixing chamber through the air ingress orifice (9). After dispensing ("stroke"), the ball valve (23), silicone seal or gasket allows entry of air external to manually-actuable, non-aerosol dispenser (25) to enter into the reservoir (3) to refill the headspace for the next stroke.

After the personal care composition and air enter into the mixing chamber (5) and form the foamed personal care composition, the foamed personal care composition exits the mixing chamber (5) via the mixing chamber egress orifice (13), traveling through a foam fluid connection (17) to the foamer assembly (1) and exits the foamer dispensing orifice (19). The foam fluid connection (17) between the mixing chamber egress orifice (13) and the foamer dispensing orifice (19) may have present therein one or more screens or meshes (21a, 21b, 21c) which may be used to modify the foam specific volume. The number of meshes, the size of the openings in the meshes and the frequency of the openings in the meshes may be used to modify the foam specific volume. In one embodiment, at least 2 meshes (21a, 21b) are utilized, wherein the 2 meshes (21a, 21b) are contiguous with each other. The meshes comprise a diameter section and a depth. The diameter section (largest surface area of the mesh) is the portion of the mesh which would be contiguous with another mesh.

At least a lower portion of the dip tube (7) may be angled toward a lowermost front corner of the reservoir (3) when the reservoir (3) is tilted at an angle for optimal squeezing and dispensing of foam, so as to maximize efficient use of the personal care composition in the reservoir (3). The angle of incline of the lowermost portion of the dip tube (7) preferably mimics the angle of incline of the foamer dispensing orifice (19), and both are preferably at an angle downward from a horizontal axis through the mesh closest to the dispensing head orifice (19) in a range of about 30° to about 45°.

In one embodiment, one to three meshes are present in the fluid connection between the mixing chamber egress and the dispensing head orifice. In one embodiment, two meshes (21a, 21b) are located in the foam fluid connection (17) in close proximity to the mixing chamber egress orifice (13), wherein the two meshes (21a, 21b) comprise about 170 micron ($\mu$) opening size and wherein one mesh (21c) is located in close proximity to the foamer dispensing orifice (19), wherein the one mesh (21c) comprises about a 70 micron (p) opening size.

In one embodiment two meshes (21a, 21b) located in the foam fluid connection (17) in close proximity to the mixing chamber egress orifice (13) and the two meshes (21a, 21b) are contiguous with each other, wherein the two meshes (21a, 21b) comprise about 170 micron (t) opening size and wherein one mesh (21c) is located in close proximity to the foamer dispensing orifice (19), wherein the one mesh (21c) comprises about a 70 micron ($\mu$) opening size. Each mesh is preferably provided as an injection molded wafer or disc having a cylindrical sidewall and a screen extending across one end of the cylindrical sidewall. The screen does not extend axially (from the top edge of the cylindrical sidewall to the bottom edge of the cylindrical sidewall moving along the y-axis) the entire length of the cylindrical sidewall. As used in this paragraph, "contiguous" means that the two cylindrical sidewalls of the respective wafers or discs are immediately adjacent one another. However, each of the respective wafers is preferably oriented with its screen is facing up, such that even with the two wafers or discs in contact with one another, there is a gap separating the screen of the first disc from the screen of the second disc.

Figure 3:
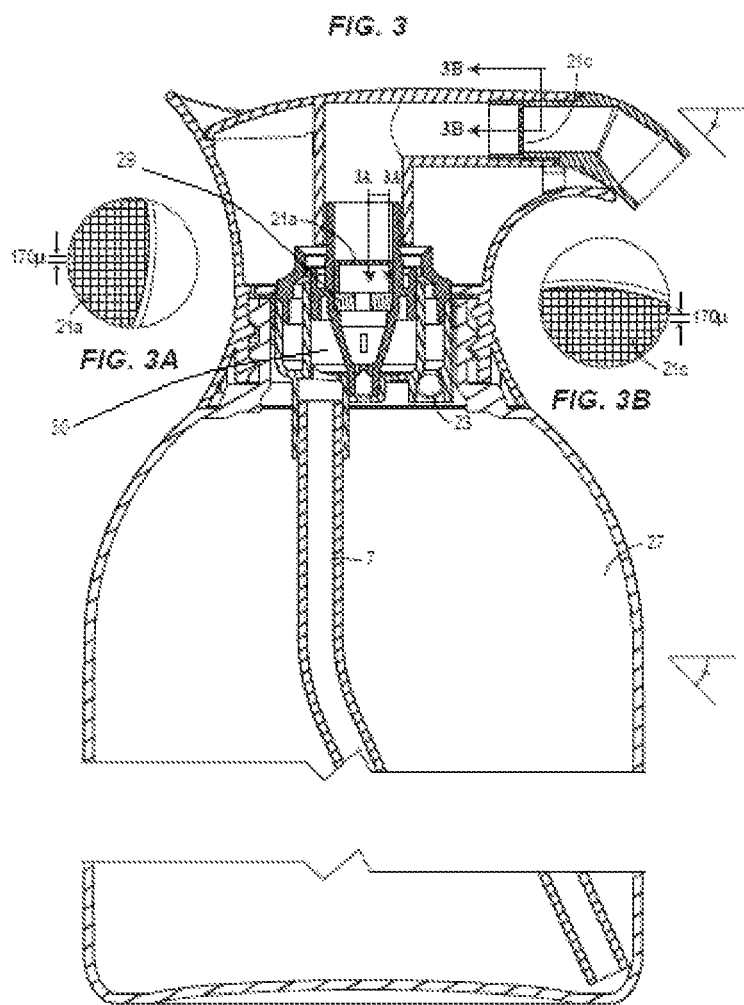
FIG. 3 is a cross-sectional view of an alternate embodiment of the manually-actuable, non-aerosol dispenser of the present disclosure.
Figure 4:
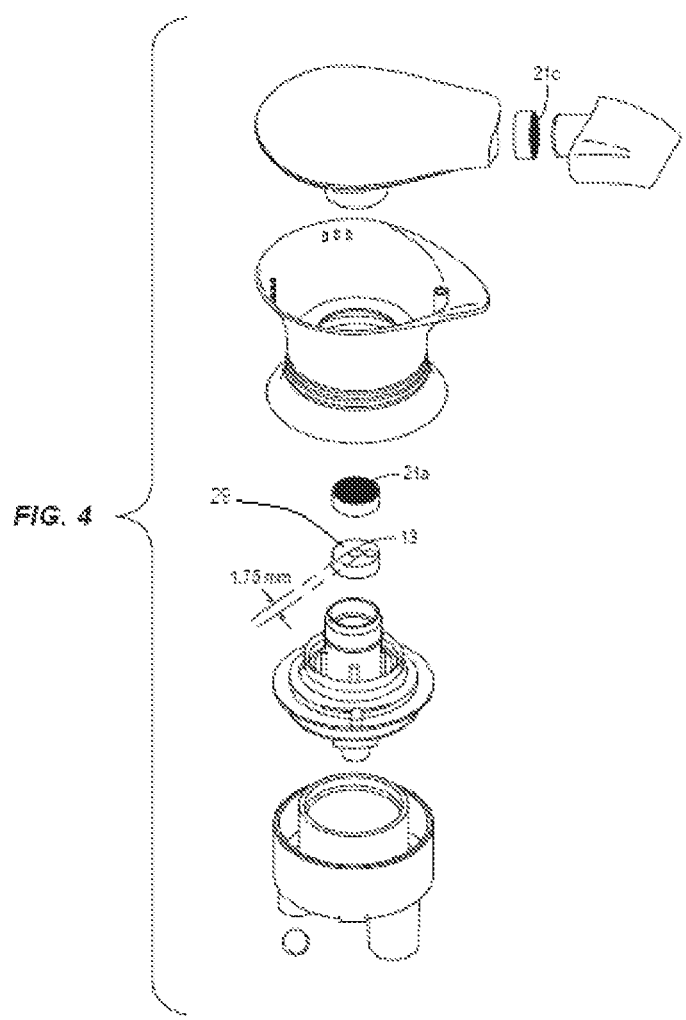
FIG. 4 is an exploded view of a dispenser head of the dispenser of FIG. 3.

Turning now to FIG. 3, a particularly preferred embodiment is illustrated in which only two meshes (21a, 21c) are utilized, one (21a) in close proximity to the mixing chamber egress orifice (13) and the other (21c) disposed close proximity to the foamer dispensing orifice (19).

By varying the size of the mixing chamber egress orifice (13), the number of meshes (21a, 21b, 21c), and the opening size of the screens of the meshes, it is possible to reduce the amount of work required to expel a desired quantity of foam, while substantially preserving the desired foam specific volume. For instance, in an exemplary implementation of the embodiment illustrated in FIG. 1, a mixing chamber egress orifice (13) of 1 mm diameter is provided in a diffuser plate (29) [area of orifice is pi*diameter]. In that embodiment, three mesh wafers or discs are provided in the foam fluid connection (17), with each of the first two (21a, 21b) comprising a mesh opening size of about 170 micron ($\mu$), and the third comprising a mesh opening size of about 70 micron (p).

In an exemplary implementation of the embodiment illustrated in FIG. 3, the second mesh (21b) is omitted, the mixing chamber egress orifice is increased to 1.75 mm in a diffuser plate (29) [area of orifice is pi*diameter], the first mesh (21a) has a mesh opening size of about 170 micron ($\mu$), and the mesh wafer or disc (21c) comprises a mesh opening size of about 70 micron ($\mu$) in located in the foam fluid connection (17).

Personal Care Composition

The manually-actuable, non-aerosol dispenser is used in combination with a personal care composition. Contemplated personal care compositions include hair colorants, body wash compositions, shampoos, conditioners, lotion, facial cleansers, cosmetics (e.g., foundation, blush, eyeshadow, skin lighteners, skin tint (aka self tanners)), perfume, shaving preparation compositions (aka shaving cream) and similar compositions.

The selection of the personal care composition will affect the desired foam properties. Rheological characteristics of the personal care composition affect the foam properties of the personal care composition after it is passed through the manually-actuable, non-aerosol dispenser. It has been found that a selected viscosity profile gives the desired foam properties when used in combination with the manually-actuable, non-aerosol dispenser described herein.

The desired viscosity profile ensures a desired consumer experience when in contact with the personal care composition. The desired mixed viscosity discussed herein results in a desired foam specific volume by preventing the alteration of the desired liquid to air ratio when too much liquid is introduced into the foam when bubbles of the personal care composition are present in the head space of the reservoir. The desired shear-thinning of the person care composition is such that the personal care composition is easily dispensed from the reservoir into a consumer's hand. In one embodiment, the low-shear viscosity of the personal care composition after the collapse of the foamed personal care composition is selected such that the composition does not drip or run from the surface on which it is applied, such as hair.

As used herein the "low-shear viscosity" of the personal care composition is measured by the method defined below.

The low-shear viscosity of the personal care composition is at least 300 cps (0.3 pascal seconds) (as measured in the methodology discussed below), preferably more than 300 cps (0.3 pascal seconds), preferably from about 400 cps (0.4 pascal seconds) to about 1500 cps (1.5 pascal seconds), preferably from about 450 cps (0.45 pascal seconds) to about 1000 cps (1.0 pascal seconds). The personal care composition may comprise components that will affect the low-shear viscosity, such as salt content. Suitable thickener should be selected to adjust the low-shear viscosity into the desired range As used herein "mixed viscosity" is the viscosity of the personal care composition where two or more components are mixed together, such as an oxidative tint and an oxidizing agent of a hair coloring composition, by a consumer just prior to use of the composition. The mixed viscosity would be the low-shear viscosity of the resulting mixture of the oxidative tint and oxidizing agent (developer composition) rather than the low-shear viscosity of the individual components of oxidative tint and oxidizing agent (developer composition) prior to mixing together. The personal care composition may comprise components that will affect the mixed viscosity, such as dyes, alkali component content or salt content. Suitable thickener should be selected to adjust the mixed viscosity into the desired range.

As examples of an impact of components on the low-shear viscosity, a personal care composition which is a hair colorant formulation comprising a high total dye content and a low alkali content represent dark shades, such a black hair colors, may have a mixed viscosity from about 500 cps (0.5 pascal seconds) to about 1000 cps (1.0 pascal seconds). Whereas, a personal care composition which is a hair colorant formulation comprising dyes relating to red shades, such as red or auburn hair colors, may have a mixed viscosity from about 400 cps (0.4 pascal seconds) to about 800 cps (0.8 pascal seconds). Further whereas, a personal care composition which is a hair colorant formulation comprising low total dye content and high alkali content representing light shades, such as blond colors, may have a mixed viscosity of from about 400 cps (0.4 pascal seconds) to about 700 cps (0.7 pascal seconds), such as 450 cps (0.45 pascal seconds) to about 700 cps (0.7 pascal seconds).

The personal care composition is desired to have the low-shear viscosity described herein. The personal care composition may comprise other components suitable for the desired end use including solvents.

For hair colorants, including oxidative and direct dye compositions, suitable components include foam generating agents, an oxidizing agent, a source of ammonium ions, oxidative dye precursors, radical scavengers, perfumes and other similar components.

For example, body wash compositions, shampoo compositions, facial cleansers, shaving preparation compositions (aka shaving cream) have foam generating agents, which may be surfactants, deposition aids and conditioning agents, perfumes and other similar components.

For example conditioners, lotion, cosmetics (e.g., foundation, blush, eyeshadow, skin lighteners, skin tint (aka self tanners)), perfume compositions include foam generating agents, cationic surfactants, conditioning agents, deposition aids, colored particulates, oxidizing agents, perfumes and similar components.

Solvents

If necessary, solvents such as water, lower aliphatic alcohols, for example aliphatic alcohols with from 1 to 4 carbon atoms such as ethanol, propanol and isopropanol, or glycols such as glycerin and 1,2-propylene glycol may be utilized for the personal care in concentrations of from 0.1 to 95% by weight of the personal care composition.

Thickeners

Suitable for use in the personal care compositions to achieve the desired mixed viscosity (as defined herein) and low-shear viscosity (as defined herein) include salts of fatty acids represented by the formula:

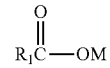

Wherein $R_1$ is a hydrocarbon radical of the formula $C_nH_{2n-1}$, $C_nH_{2n-1}$ or $C_nH_{2n-3}$ and n is an integer from 12 to 24. M is hydrogen, sodium, potassium and ammonium. Examples include ammonium stearate, potassium stearate, ammonium oleate and ammonium ricinoleate. Ammonium salts may result from in-situ formation from fatty acids and ammonia, such as oleic acid and ammonia.

The salts of fatty acids may be present in the tint composition from about 0.05% to about 10%, such as about 0.1% to about 8%, such as from about 1% to about 5% by weight of the tint composition.

Polysaccharides and copolymers of polysaccharides and synthetic monomers are also useful as thickeners. Such saccharides useful herein include: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above saccharides. Xanthan gum, e.g., CP Kelco's KELTROL® T, (molecular weight about 2,000,000) is also a suitable polymer. Also suitable include gellan gum (e.g., CP Keloc's KELCOGEL® AFT), pectine, alginate, arabinogalctan, carageenan, rhamsan gum and furcellaran gum. Suitable for use as a thickener herein include cellulose derivatives such as hydroxyethyl- and carboxymethylcellulose and guar gums such as hydroxypropyltrimethyl ammonium guar gum. Specific examples include: a nonionic hydroxyethyl cellulose polymers (e.g., Aqualon/Hercules Incorporated's NATROSOL® 250MXR and NATROSOL® 250HR); and cationic hydroxyethyl cellulose polymers (e.g., Union Carbide Corporation's JR-400 and LM-200).

Some additional polymers suitable for use as a thickener include polyvinyl pyrrolidone and copolymers of vinylpyrrolidone such as those containing vinyl acetate, dimethylaminoethylmethacrylate and quaternary versions of the same with methyl sulfates, and polymers and copolymers of vinyl alcohol and vinyl acetate. Some acrylic polymers suitable for use herein include polyacrylic acid (e.g., Noveon's CARBOPOL® polymers), polyacrylamide, copolymers with esters of acrylic acid and methacrylic acid and copolymers of methylvinylether and maleic anhydride.

Further suitable thickeners are listed in the Glossary and Chapters 3 (alkyl and hydroxyalkylakylcellulose), 4 (carboxymethylcellulose), 12 (hydroxyethylcellulose) and 13 (hydroxypropylcelluose) of the Handbook of Water-Soluble Gums and Resins. Robert L. Davidson, McGraw-Hill Book Co., New York, N.Y., 1980.

The amount of polymeric thickener found useful in the personal care compositions is about 0.1% to about 20%, preferably from about 0.1% to about 10% by weight of the personal care composition.

Foaming Agent

The foaming agent may be anything so long as it has foaming properties including surfactants such as nonionic, anionic, cationic and amphoteric surfactants. Preferred foaming agents include amphoteric surfactants.

Useful anionic surfactants in hair colorant compositions include alkyl ether carboxylates, alkyl ether sulphates, alkyl glyceryl sulphonates, alkylamido ether sulphates, alkylarylpolyether sulphates, alkyl monoglyceride sulphates, alkyl ether sulphonates, alkylamide sulphonates; alkyl succinates, alkyl sulphosuccinates, alkyl ether sulphosuccinates, alkylamide sulphosuccinates; alkyl sulphosuccinamates; alkyl sulphoacetates; alkyl ether phosphates; acyl sarcosinates, N-acyl methylaminopropionate; acyl isethionates, N-acyltaurates; acyl lactylates; carboxyalkyl ether of alkyl polyglucosides; alkyl lecithin derivatives. In one embodiment, an anionic surfactant is selected as C8-C30 alkyl ether phosphates having from 1 to 20, preferably 2 to 10 ethylene oxide units, and a non-ionic surfactant selected from polyoxyethylene alkyl ethers having at least 25, preferably from 100 to 200 ethylene oxide units.

Further nonionic surfactants useful in hair colorant compositions include one or more polyethyleneoxide chains include the following compounds: polyoxyethylene alkyl ethers, polyethyleneglycol fatty acid esters, polyoxyethylene castor oil, polyoxyethylene hydrogenated castor oil, polyoxyethylene fatty amides and their momoethanolamine and diethanolamine derivatives and polyethoxylated fatty amines. In one embodiment include polyoxyethylene alkyl ethers or polyethylene glycol fatty acid esters having at least about 25, preferably from about 50 to 200, most preferably from about 100 to 200 ethylene oxide units, for example ceteareth-25, steareth-100, steareth-150 and steareth-200.

Useful surfactants in body wash compositions, shampoo compositions and facial cleanser compositions include alkyl sulfates and alkyl ether sulfates have the formula: $RO(C_2H_4O)_xSO_3M$, wherein R is alkyl or alkenyl of from about 8 to about 24 carbon atoms, x is 0 to 10, such as 0 (for alkyl sulfates) or 0.1 to 3; and M is a cation such as ammonium, alkanolamines, such as triethanolamine, monovalent metals, such as sodium and potassium, and polyvalent metal cations, such as magnesium, and calcium. Preferably, R has from about 8 to about 18 carbon atoms, more preferably from about 10 to about 16 carbon atoms, most preferably from about 12 to about 14 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm kernel or tallow, or can be synthetic. Lauryl alcohol and straight chain alcohols derived from coconut oil or palm kernel are preferred herein. Such alcohols are reacted with between about 1 and about 10, and especially about 1 to about 3, molar proportions of ethylene oxide and the resulting mixture of molecular species having, for example, an average of 3 moles of ethylene oxide per mole of alcohol, is sulfated and neutralized.

Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Preferred surfactants for use in shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Further suitable surfactants for body wash compositions and facial cleanser compositions include amphoteric surfactants. Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention. Most preferred for use herein is cocoamidopropyl betaine.

Nonionic surfactants useful include those selected from the group consisting of alkyl glucosides, alkyl polyglucosides, polyhydroxy fatty acid amides, alkoxylated fatty acid esters, lathering sucrose esters, amine oxides, and mixtures thereof. Alkyl glucosides and alkyl polyglucosides are useful herein, and can be broadly defined as condensation articles of long chain alcohols, e.g., C3-C30 alcohols, with sugars or starches or sugar or starch polymers, i.e., glycosides or polyglycosides. These compounds can be represented by the formula (S)nOR wherein S is a sugar moiety such as glucose, fructose, mannose, and galactose; n is an integer of from about 1 to about 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like.

Useful surfactants for hair colorant compositions are discussed in US 20040213752 in paragraphs [0024]-[0027]. The amount of surfactant found useful in the hair colorant compositions is about 0.1% to about 20%, preferably from about 0.1% to about 10% by weight of the hair colorant composition.

Concentration of such surfactants in the body wash composition, shampoo compositions or facial cleanser compositions may be from about 0.5% to about 35%, preferably from about 1% to about 25%, more preferably from about 2% to about 25% by weight of the composition.

Suitable foaming agents include polymeric foam stabilizers and polymeric emulsifiers. Polymeric foam stabilizers and polymeric emulsifiers may be used with surfactants or may be used without surfactants. Combinations of polymeric emulsifiers and polymeric foam stabilizers are also embodied herein.

Polymeric Foam Stabilizers

Polymeric foam stabilizing agents suitable for use herein include cellulose materials such as methylcellulose (hydroxypropyl methylcellulose sold as METHOCEL 40-101 and methylcellulose sold as METHOCEL A4MP) and ethylcellulose (Cecetyl hydroxyethylcellulose sold as NATROSOL PLUS).

The hydroxypropyl methylcellulose may have the general structure of:

2% aqueous solution at 20° C. with a Ubbelohde tube viscometer).

Another suitable foam stabilizing agent includes (meth) acrylic polymers such as Acrylates/$C_{10-30}$ alkyl acrylate crosspolymer, a copolymer of $C_{10-30}$ alkyl acrylates and one or more monomers of acrylic acid, methacrylic acid or one of their simple esters crosslinked with an allyl ether of sucrose or an allyl ether of pentaerythritol. It is commercially available from Goodrich as PEMULEN TR-1 and PEMULEN TR-2. PEMULEN TR-1 polymer is preferred. CAPIGEL 98, an acrylates copolymer produced by SEPPIC.

Another suitable foam stabilizing agent suitable for use herein is a hydrophobically-modified alkali soluble emulsion polymer synthesized through an emulsion polymerization process from an acid/acrylate copolymer backbone and a monomer that connects the hydrophobic groups as side chains. An example of such a material is ACULYN™ 22, commercially available from Rohm Haas with an INCI name of Acrylates/Steareth-20 Methacrylate Copolymer.

Another suitable foam stabilizing agent includes anionic alkali-soluble polymer emulsion synthesized from acid and acrylate co-monomers through emulsion polymerization. An example of such a material is ACULYN™ 33, commercially available from Rohm Haas with an INCI name of Acrylates Copolymer.

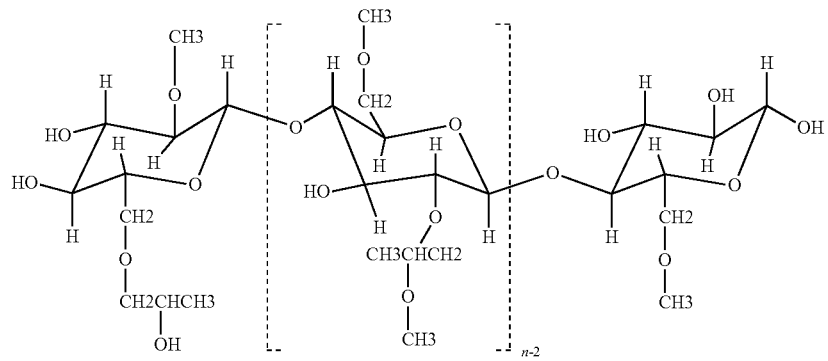

The methylcellulose may have the general structure of:

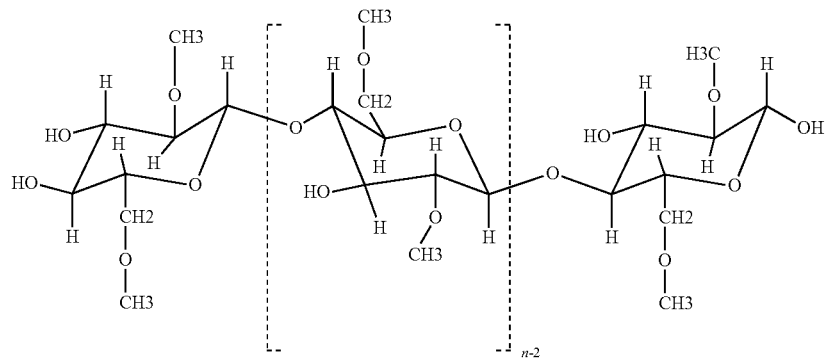 [SMILES: COCC1OC(OC2C(COC)OC(OC3C(COC)OC(O)C(OC)C3O)C(OC)C2O)C(OC)C(O)C1O]

The "n" of these structures is selected to give the desired viscosity. The METHOCEL 40-101 has a viscosity of about 75,000 mPa s (for a 2% aqueous solution at 20° C. with a Ubbelohde tube viscometer) and the METHOCEL A4MP has a viscosity of about 4000-5000 mPa s (for a Mixtures of ACULYN™ 22 and ACULYN™ 33 may be used. One embodiment utilizes a mixture of ACULYN™ 22 and ACULYN™ 33 in a ratio (weight) of 1:2 to 1:5 weight ratio based upon the weight of the personal care composition or based upon the weight of the developer composition of a hair colorant composition. In one embodiment, a mixture of ACULYN™ 22 and ACULYN™ 33 in a ratio (weight) of 1:3 to 1:4 by weight of the developer composition of a hair colorant composition is utilized.

Polyquaternium-55, a polymer comprising vinyl pyrrolidone (VP), dimethylaminopropyl methacrylamide (DMAPA) and methacryoylaminopropyl lauryldimonium chloride (MAPLAC) is also suitable for use herein and has the following generalized structure:

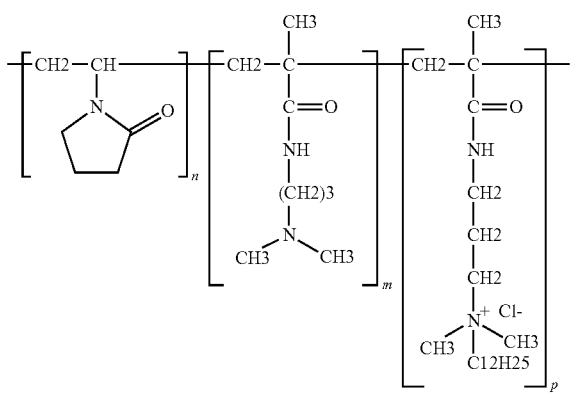

Polyquaternium-55 is sold under the tradename STYLEZE® in a 10 and 20 variation. The n, m and p levels depend on the monomer ratio. The STYLEZE®-10 has a monomer ratio of 0.85VP:0.11DMAPA:0.4MAPLAC. The STYLEZE®-20 has a monomer ratio of 0.85VP:0.11DMAPA:0.4MAPLAC.

Another suitable foam stabilizing agent includes a polyoxyethylene, polyoxypropylene block polymer that conforms generally to the formula shown below in which the average values of x, y and z are respectively 31, 54 and 31.

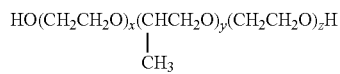

sold under the tradename POLOXAMER 334.

Another suitable foam stabilizing agent includes a polyethyleneoxide-polypropyleneoxide-polyethyleneoxide block polymer terminating in primary hydroxyl groups sold under the tradename PLURONIC P104 and PLURONIC F108 (ex. BASF).

Polymeric Emulsifiers

Suitable a polymeric emulsifing agents include polysaccharides, cellulosic materials, amine-bearing polymers, acidic polymers obtainable from natural sources, chemically modified starches, carboxyvinyl polymers, polyvinylpyrrolidone, polyvinyl alcohol, polyacrylic acid polymers, polymethacrylic acid polymers, polysiloxanes and mixtures thereof.

Suitable polysaccharides include xanthan gum, carrageenin gum, guar-guar, cationic guars, hydroxypropyl guar gum, agar-agar, locust bean gum, alginates, tyloses, salts of any of these materials (such as sodium salts) and mixtures thereof.

Suitable cellulosic materials include cellulose ethers, such as carboxymethylcellulose, ethylcellulose, hydroxypropylcellulose, methylcellulose, cellulose mixed ethers, such as carboxymethylhydroxyethylcellulose, ethylhydroxyethylcellulose, methoxyhydroxyalkylcelluloses, methylhydroxyalkylcelluloses, such as methylhydroxyethylcellulose, methylhydroxypropylcellulose, methylhydroxybutylcellulose; and mixtures of these.

Suitable amine-bearing polymers include deacytylated chitin, sometimes known as chitosan, which as been modified to be soluble in basic conditions usually by alkylation or by carboxymethylation, but other modifications of chitin are also suitable. See *Chitosan Derivatives Obtained By Chemical Modifications For Biomedical And Environmental Applications*; International Journal of Biological Macromolecules; Volume 43, Issue 5, 1 Dec. 2008, Pages 401-414.

Suitable polysiloxanes include dimethylpolysiloxanes, methylphenylpolysiloxanes, cyclic silicones as well as silicone compounds modified by amino, fatty acid, alcohol, polyether, epoxy, fluoro, glycoside and or alkyl groups. Preferred as silicone compounds according to the present invention are polysiloxane-polyether copolymers aka dimethicone copolyol, which are available from the company named Goldschmidt AG of Essen under the trade name ABIL®, especially polysiloxane-polyether copolymers of the B 88 product family, such as ABIL® B 8843, ABIL® B 8851, ABIL® B 8852, ABIL® B 8863, ABIL® B 88183 and ABIL® B 88184.

The polymeric foam stabilizers and polymeric emulsifiers to be dispensed in the personal care composition in an amount sufficient to allow formation and/or stabilization of foam, either with or without a surfactant. Generally, the polymeric foam stabilizers and polymeric emulsifiers will be present in an amount of from 1 to 25% by weight, preferably 2 to 15% by weight, more preferably 2 to 10% by weight of the personal care composition.

Perfume

The personal care compositions may comprise a perfume component or components. Perfumes are often a mixture of components such as essential oils, aroma compounds and solvents (ethanol, water and perfume oils, such as jojoba oil) to provide a sensorial experience with top, middle and base notes selected for the personal care composition. Such components may be found in "Perfume and Flavor Chemicals (Aroma Chemicals)," Steffen Arctander, published by the author, 1969.

Cationic Deposition Polymers

The personal care composition may comprise a cationic deposition polymer selected from cellulose, guar, cationically modified starch, galactomannan polymer derivative and suitable synthetic deposition polymers.

Cellulose or Guar Cationic Deposition Polymers

The personal care compositions of the present invention may include cellulose or guar cationic deposition polymers. Such cellulose or guar deposition polymers have a charge density from about 3 meq/g to about 4.0 meq/g at the pH of intended use of the personal care composition, which pH will generally range from about pH 3 to about pH 9, preferably between about pH 4 and about pH 8. The pH of the compositions of the present invention are measured neat.

In one embodiment of the invention, the cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA).

Other suitable cationic deposition polymers include cationic guar gum derivatives, such as guar hydroxypropyltrimonium chloride, specific examples of which include the Jaguar series (preferably Jaguar C-17®) commercially available from Rhone-Poulenc Incorporated.

Cationically Modified Starch Polymer

The personal care compositions may also comprise a water-soluble cationically modified starch polymer. The cationically modified starch polymers have a charge density at least about 3.0 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof. Waxy corn starch is preferred.

Galactomannan Polymer Derivative

The personal care compositions of the present invention may comprise a galactomannan polymer derivative having a mannose to galactose ratio of greater than 2:1 on a monomer to monomer basis, the galactomannan polymer derivative is selected from the group consisting of a cationic galactomannan polymer derivative and an amphoteric galactomannan polymer derivative having a net positive charge.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose). Herein, the term "non-guar galactomannan polymer derivatives" refers to cationic polymers which are chemically modified from a non-guar galactomanan polymer. A preferred non-guar galactomannan polymer derivative is cationic cassia, which is sold under the trade name, Cassia EX-906, and is commercially available from Noveon Inc.

The personal care compositions may comprise at least about 0.05% of a galactomannan polymer derivative by weight of the composition. In one embodiment, the personal care compositions comprise from about 0.05% to about 2%, by weight of the composition, of a galactomannan polymer derivative. Suitable galactomannan polymer derivatives are described in U.S. Patent Publication No. 2006/0099167A1 to Staudigel et al.

Synthetic Deposition Polymers

Synthetic deposition polymers may also be used in the personal care composition from about 0.05% to about 2% by weight of the personal care composition. Suitable synthetic deposition polymers include those discussed in U.S. Pat. No. 7,585,827, specifically discussed at Col. 5, lines 1-67 and Col. 8, line 5-Col 15. line 5. The synthetic polymer of 1-Propanaminium, N,N,N-trimethyl-3-[(2-methyl-1-oxo-2-propenyl)amino]-, chloride; (Poly(Methacrylamidopropyl trimethyl ammonium chloride)) is a preferred synthetic polymer.

Another synthetic polymers suitable for the personal care composition include those discussed in US 2004/0010106 and US 2007/0207109. A particularly suitable synthetic polymer is a random copolymer having a net positive charge comprising a nonionic monomer unit of the following formula:

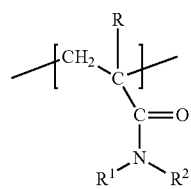

where R is H or $C_{1-4}$ alkyl; and $R^1$ and $R^2$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and a cationic monomer unit with 2 or more positive charges of the following formula:

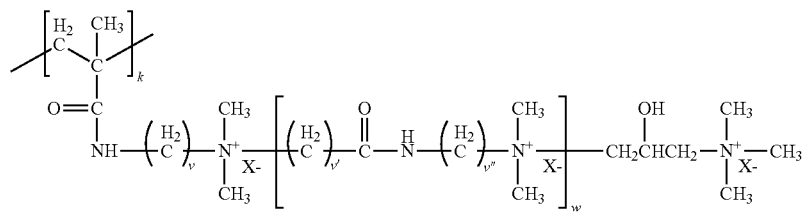

where k=1, each of v, v', and v" is independently an integer of from 1 to 6, w is zero or an integer of from 1 to 10, and $X^-$ is an anion. A preferred cationic monomer is when k=1, v=3, v'=1, and v"=3, w=1, y=1 and X– is Cl— (see paragraph [0051] of US 2007/0207109).

Exfoliating Agents

The bodywash compositions and facial cleanser composition may further comprise particulate cleansing or exfoliating agents. Known particulate cleansing or exfoliating agents are acceptable as long as the particle size is suitable for use with the manually-actuable, non-aerosol dispensers and the components thereof, such as the porous elements.

Conditioning Agent

The personal care composition may comprise or are used in combination with a conditioning composition comprising a conditioning agent. Conditioning agents suitable are selected from silicone materials, amino silicones, fatty alcohols, polymeric resins, polyol carboxylic acid esters, cationic polymers, cationic surfactants, insoluble oils and oil derived materials and mixtures thereof. Additional materials include glycerin and sorbitol. Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain or mixtures thereof. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion.

The conditioning agent will generally be used at levels of from about 0.05% to about 20% by weight of the personal care composition, such as from about 0.1% to about 15%, such as of from about 0.2% to about 10%, such as from about 0.2% to about 2% by weight of the personal care composition.

Hair Colorant Composition Components

The hair colorant composition contains an oxidative tint composition (herein after tint composition) comprising oxidative dye precursors, through which the coloring is produced by the action of oxidizing agents (present as a developer composition), such as for example hydrogen peroxide, or in the presence of atmospheric oxygen (if necessary with the addition of a suitable enzyme system).

Generally, the weight ratio of tint formulation:developer formulation for a hair colorant composition is in the range 5:1 to 1:5, such as 1:1, 1:1.5, 1:2, 1:3 and 1.4 depending on strength of developer composition and tint composition.

Oxidative Dye Precursors

The hair colorant compositions may include oxidative dye compounds in the form of primary intermediates or couplers. The compounds suitable for use, in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic hydroxyl groups, in the form of their salts with bases, such as alkali phenolates.

These oxidative dye compounds are well known in the art, and include aromatic diamines, aminophenols, aromatic diols and their derivatives (a representative but not exhaustive list of oxidation dye precursor can be found in Sagarin, "Cosmetic Science and Technology", "Interscience, Special Edn. Vol. 2 pages 308 to 310).

It is to be understood that the precursors detailed below are only by way of example and are not intended to limit the hair care compositions or sub-components such as tint compositions herein. These are: 1,7-Dihydroxynaphthalene (1,7-NAPHTHALENEDIOL); 1,3-Diaminobenzene (m-PHENYLENEDIAMINE); 1-Methyl-2,5-diaminobenzene (TOLUENE-2,5-DIAMINE); 1,4-Diaminobenzene (p-PHENYLENEDIAMINE); 1,3-Dihydroxybenzene (RESORCINOL); 1,3-Dihydroxy-4-chlorobenzene, (4-CHLORORESORCINOL); 1-Hydroxy-2-aminobenzene, (o-AMINOPHENOL); 1-Hydroxy-3-aminobenzene (m-AMINOPHENOL); 1-Hydroxy-4-amino-benzene (p-AMINOPHENOL); 1-Hydroxynaphthalene (1-NAPHTHOL); 1,5-Dihydroxynaphthalene (1,5-NAPHTHALENEDIOL); 2,7-dihydroxynaphthalene (2,7-NAPHTHELENEDIOL); 1,4-Dihydroxybenzene (HYDROQUINONE); 1-Hydroxy-4-methylaminobenzene (p-METHYLAMINOPHENOL); 6-Hydroxybenzo-morpholine (HYDROXYBENZOMORPHOLINE); 1-Methyl-2-hydroxy-4-aminobenzene (4-AMINO-2-HYDROXY-TOLUENE); 1-Methyl-2-hydroxy-4-(2'-hydroxyethyl)aminobenzene (2-METHYL-5-HYDROXY-ETHYLAMINO-PHENOL); 1,2,4-Trihydroxybenzene (1,2,4-TRIHYDROXYBENZENE); 1-Phenol-3-methylpyrazol-5-on (PHENYLMETHYLPYRAZOLONE); 1-(2'-Hydroxyethyloxy)-2,4-diaminobenzene (2,4-DIAMINOPHENOXY-ETHANOL HCL); 1-Hydroxy-3-amino-2,4-dichlorobenzene (3-AMINO-2,4-DICHLORO-PHENOL); 1,3-Dihydroxy-2-methylbenzene (2-METHYLRESORCINOL); 1-Amino-4-bis-(2'-hydroxyethyl)aminobenzene (N,N-BIS(2-HYDROXY-ETHYL)-p-PHENYLENE-DIAMINE); 2,4,5,6-Tetraminopyrimidine (HC Red 16); 1-Hydroxy-3-methyl-4-aminobenzene (4-AMINO-m-CRESOL); 1-Hydroxy-2-amino-5-methylbenzene (6-AMINO-m-CRESOL); 1,3-Bis-(2,4-Diaminophenoxy)propane (1,3-BIS-(2,4-DIAMINO-PHENOXY)-PROPANE); 1-(2'-Hydroxyethyl)-2,5-diaminobenzene (HYDROXYETHYL-p-PHENYLENE DIAMINE SULPHATE); 1-Methoxy-2-amino-4-(2'-hydroxyethylamino)benzene, (2-AMINO-4-HYDROXY-ETHYLAMINOANISOLE); 1-Hydroxy-2-methyl-5-amino-6-chlorobenzene (5-AMINO-6-CHLORO-o-CRESOL); 1-Hydroxy-2-amino-6-methylbenzene (6-AMINO-o-CRESOL); 1-(2'-Hydroxyethyl)-amino-3,4-methylenedioxybenzene (HYDROXYETHYL-3,4-METHYLENEDIOXY-ANILINE HCl); 2,6-Dihydroxy-3,4-dimethylpyridine (2,6-DIHYDROXY-3,4-DIMETHYLPYRIDINE); 3,5-Diamino-2,6-dimethoxypyridine (2,6-DIMETHOXY-3,5-PYRIDINEDIAMINE); 5,6-Dihydroxyindole (5,6-DIHYDROXY-INDOLE); 4-Amino-2-aminomethylphenol (2-AMINOETHYL-p-AMINO-PHENOL HCl); 2,4-Diamino-5-methylphenetol (2,4-DIAMINO-5-METHYL-PHENETOLE HCl); 2,4-Diamino-5-(2'-hydroxyethyloxy) toluene (2,4-DIAMINO-5-METHYLPHENOXYETHANOL HCl); 5-Amino-4-chloro-2-methylphenol (5-AMINO-4-CHLORO-o-CRESOL); 1,3-Bis(N(2-Hydroxyethyl)N(4-amino-phenyl)amino)-2-propanol (HYDROXYPROPYL-BIS-(N-HYDROXYETHYL-p-PHENYLENEDIAMINE)HCL); 6-Hydrorxyindole (6-HYDROXY-INDOLE); 2,3-Indolinedione (ISATIN); 3-Amino-2-methylamino-6-methoxypyridine (HC BLUE NO. 7); 1-Phenyl-3-methyl-5-pyrazolone (2,4-DIHYDRO-5-METHYL-2-PHENYL-3H-PYRAZOL-3-ONE); 2-Amino-3-hydroxypyridine (2-AMINO-3-HYDROXYPYRIDINE); 5-Amino-salicylic acid; 1-Methyl-2,6-bis(2-hydroxy-ethylamino)benzene (2,6-HYDROXYETHYLAMINO-TOLUENE); 4-Hydroxy-2,5,6-triaminopyrimidine (2,5,6-TRIAMINO-4-PYRIMIDINOL SULPHATE); 2,2'-[1,2-Ethanediyl-bis-(oxy-2,1-ethanediyloxy)]-bis-benzene-1,4-diamine (PEG-3,2',2'-DI-p-PHENYLENEDIAMINE); 5,6-Dihydroxyindoline (DIHYDROXYINDOLINE); N,N-Dimethyl-3-ureidoaniline (m-DIMETHYL-AMINO-PHENYLUREA); 2,4-Diamino-5-fluortoluenesulfatehydrate (4-FLUORO-6-METHYL-m-PHENYLENEDIAMINE SULPHATE); 1-Acetoxy-2-methylnaphthalene (1-HYDROXYYETHYL-4,5-DIAMINOPYRAZOLE SULPHATE); 1-acetoxy-2-methylnaphthalene (2-METHYL-1-NAPHTHOL); 2-amino-5-ethylphenol (2-AMINO-5-ETHYLPHENOL); 2,4-dichloro-3-aminophenol (3-AMINO-2,4-DICHLOROPHENOL); and p-Anilinoaniline (N-PHENYL-P-PHENYLENEDIAMINE).

The total quantity of the oxidative dye precursors contained in tint composition is up to about 12 percent by weight, especially from about 0.05% to about 6% by weight of the tint composition.

To obtain specific color shades, moreover, additional conventional natural and/or synthetic direct dyes can be contained in the colorant, for example plant pigments such as henna or indigo, triphenylmethane dyes, aromatic nitro dyes, azo dyes, quinone dyes, cationic dyes (Basic dyes) or anionic dyes (Acid dyes).

Alkalizing Agent

The tint composition comprises an alkalizing agent, preferably a source of ammonium ions and or ammonia. Any alkalizing agent known in the art may be used such as alkanolamides for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol and guanidium salts. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia and mixtures thereof.

The tint compositions may comprise from about 0.1% to about 10% by weight, such as from about 0.5% to about 5%, such as from about 1% to about 3% of an alkalizing agent, such as a source of ammonium ions.

Oxidizing Agent

The hair colorant compositions herein, generally in the developer composition, may comprise at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water.

The oxidizing agent may be selected from water-soluble oxidizing agents which are inorganic peroxygen materials capable of yielding hydrogen peroxide in an aqueous solution. The oxidizing agents may be provided in aqueous solution or as a powder which is dissolved prior to use. Water-soluble oxidizing agents include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can also be used if desired. Preferred for use in the compositions according to the present invention are hydrogen peroxide, percarbonate, persulphates and combinations thereof.

The oxidative agent may comprise from about 0.1% to about 40% by weight, preferably from about 1% to about 30% by weight, and most preferably from about 2% to about 30% by weight of the hair colorant composition or developer composition. Another potential oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH (of the hair care composition) of up to and including 9.5, preferably 7.5 to 9.5 more preferably about pH 9. Moreover, this system is also particularly effective in combination with a source of ammonia or ammonium ions.

Accordingly, any source of these peroxymonocarbonate ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and as an oxidizing agent. Preferred sources of carbonate ions, carbamate and hydrocarbonate ions are sodium hydrogen carbonate, potassium hydrogen carbonate, ammonium carbamate, and mixtures thereof.

The oxidative agent may comprise from about 0.1% to about 15% by weight, preferably from about 1% to about 10% by weight, and most preferably from about 1% to about 8% by weight of a hydrogencarbonate ion and from about 0.1% to about 10% by weight, preferably from about 1% to about 7% by weight, and most preferably from about 2% to about 5% by weight of the oxidative agent of a source of hydrogen peroxide.

Chelants

The hair colorant compositions or sub-components thereof (such as a tint composition or developer composition) comprise a carboxylic acid chelant, a phosphonic acid chelant, a polyphosphoric acid chelant, salts thereof, or mixtures thereof. Suitable chelants include diethylenetriamine pentaacetic acid (DTPA), ethylenediamine-N,N'-disuccinic acid (EDDS), ethylenediamine-N,N'-diglutaric acid (EDDG), 2-hydroxypropylenediamine-N,N'-disuccinic acid (HP-DDS), glycinamide-N,N'-disuccinic acid (GADS), ethylenediamine-N—N'-bis(ortho-hydroxyphenyl acetic acid) (ED-DHA), diethylene-triamine-penta-(methylenephosphonic acid) (DTPMP), salts thereof, derivatives thereof, or mixtures thereof.

The hair colorant composition or sub-component thereof, such as the tint composition, comprise from about 0.01% to about 5%, from about 0.25% to about 3%, from about 0.5% to about 1% by weight of the hair colorant composition, or sub-component thereof of chelant, salts thereof, derivatives thereof, or mixtures thereof.

Radical Scavenger

The hair colorant compositions may further comprise a source of radical scavenger. Suitable radical scavengers for use herein may be selected from the classes of alkanolamines, amino sugars, amino acids, esters of amino acids and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof. Especially preferred compounds are glycine, sarcosine, lysine, serine, 2 methoxyethylamine, glucosamine, glutamic acid, morpholine, piperidine, ethylamine, 3 amino-1-propanol and mixtures thereof.

The hair colorant compositions preferably comprise from about 0.1% to about 10% by weight, preferably from about 1% to about 7% by weight of the hair colorant composition or sub-component thereof, such as a tint composition, of a radical scavenger.

Preferably, the radical scavenger is present at an amount such that the weight ratio of radical scavenger to carbonate ion (or peroxymonocarbonate ion) is from 2:1 to 1:4. The radical scavenger is also preferably selected such that it is not an identical species as the alkalizing agent.

pH

The hair colorant compositions of the present invention may have a pH of from 8 to 12, preferably from 8 to 10. For embodiments comprising a peroxymoncarbonate ion the pH is preferably up to and including pH 9.5, more preferably from about 9.5 to about 7.5, even more preferably from about 9.5 to about 8.4 and most preferably from about 9.4 to about 8.5 and even more preferably about pH 9.3 or 9.0.

Any sub-components of the hair colorant compositions, such as a tint composition or a developer composition may have a different pH from the hair colorant composition. For example, if the tint composition comprises an alkalizing agent, the tint composition will have an alkaline pH, such as higher than 8.

The pH of the compositions can be determined by using either a Mettler Toledo MP220 or a MP225 pH equipment, fitted with a standard laboratory pH electrode. The equipment is calibrated before each use using standard calibration buffers and using the standard calibration procedure.

Test Methods

Viscosity

Low-Shear Viscosity

The low-shear viscosity is measured via a TA Instruments AR2000 Rheometer having the following geometry:
- 40 mm 2° stainless steel cone
- 40 mm stainless steel plate
- Standard Size DIN or Conical Concentric Cylinders Using the data analysis program of the TA Instruments AR2000 Rheometer, collected data is then graphed and a point at the beginning of the run is recorded as the low-shear viscosity. Data should be run at least twice to ensure correlation of the recorded data.

For products requiring a mixed viscosity (as defined above) resulting from two different components to make the personal care composition, the low-shear viscosity can be measured as above after the following sample preparation.

Sample Preparation—Hair Colorant Composition

A tint composition and a developer composition are combined to make an hair colorant composition. The sample preparation of the hair colorant composition should be as follows:

1. combine, in a 1:1 weight ratio, the tint composition and the developer composition in a closable container from which it can be dispensed. The container should be closed or capped.
2. the closable container is then placed into a Mechanical Mixer (described below) and is shaken for 15 seconds.
3. The contents of the closed container poured into a 100 tall container available from FlackTek Inc. is then placed onto a DAC 800 FVZ SpeedMixer from FlackTek Inc. set to 1950 rpm for 10 seconds to draw any bubbles in the out of the sample.
4. A watch glass is used to contain the bubbles or foam on the top of the sample, while the liquid is decanted into a container suitable for measuring viscosity.
5. The sample is then measured for viscosity.

Mechanical Mixer

The Mechanical Mixer (31) is a device to replicate a shaking motion of a consumer. By shaking motion, it is a motion using the elbow as a pivot (fulcrum) point, with the wrist in a straight position and the arm is moved about the pivot point in an up and down motion.

Figure 5:
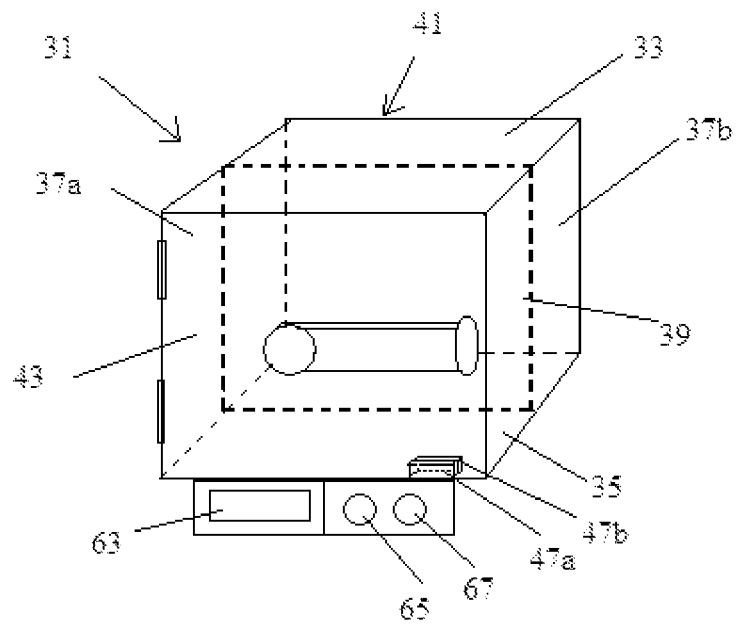
FIG. 5 is a perspective view of the mixing device described for the viscosity test method below.

The Mechanical Mixer (31) in FIG. 5 is an enclosed device having a top wall (33), a bottom wall (35), two vertical side walls (37a, 37b), a middle panel (39), a back panel (41) and a hinged door (43) which hingeably opens and shuts to allow access to the enclosed device. A metal bar (45), described further below, and a door safety switch (47) are located on one side of the middle panel (39) between the middle panel (39) and the hinged door (43). A air controlled solenoid motor (49), electrical air dump mechanism (51), air regulator (53), power supply (55) and safety relay (57) are located on a second side of the middle panel (43) between the middle panel (43) and the back panel (41).

Figure 6:
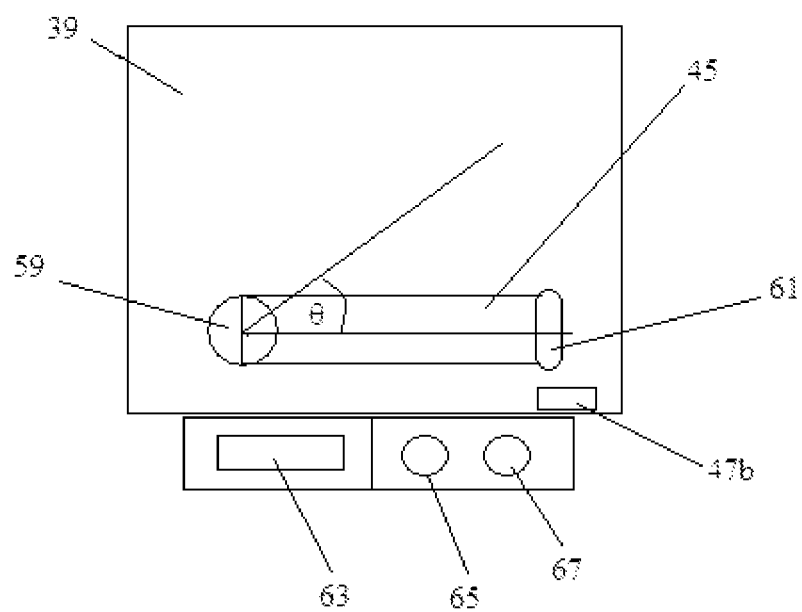
FIG. 6 is a front view of the mixing device described for the viscosity test method below.

The Mechanical Mixer (31) from a view shown in FIG. 6 (which does not shown the hinged door (43), top wall (33), bottom wall (35) or two vertical side walls (37a, 37b)) comprises a 45.16 cm length metal bar (45) having a pivot point (59) on one end of the bar (45) and a clamping means (61) on a second end of the bar (45) that is capable of holding a container of the oxidative hair colorant composition while the Mechanical Mixer (31) is in operation. The metal bar (45) should travel in an upwards and downwards direction through a 44° angle (34.5 cm arc) shown as θ. The pivot point (59) is moved through the desired angle via an air controlled solenoid motor (49) capable of 45 cycles (up and down motion) in 15 seconds.

Figure 7:
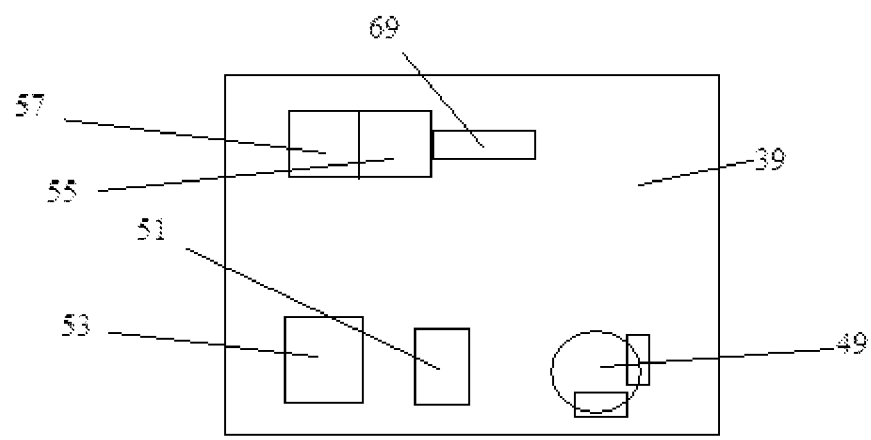
FIG. 7 is a back view of the mixing device described for the viscosity test method below.

In FIG. 7 (which does not shown the back panel (41), top wall (33), bottom wall (35) or two vertical side walls (37a, 37b)), the air controlled solenoid motor (49) can be see and is connected to an electrical air dump mechanism (51). The air dump mechanism (51) is connected to an air regulator (53), which generates the air pressure to drive the air controlled solenoid motor (49). The air regulator (53) is connected to a power supply (55) and preferably a safety relay (57) as there is a pressurized air system for the Mechanical Mixer (31). The safety relay (57) is connected to a door safety switch (47), comprising two halves (47a, 47b), the first half (47a) is located partially on the hinged door (43) and the second half (47h) is inside the space enclosed by the top wall (33), bottom wall (35), two vertical walls (37a, 37b), the middle panel (39) and the hinged door (43), the two halves (47a, 47b) being located adjacent to each other in order to complete a circuit with the safety relay (57). When the two halves (47a, 47b) of the door safety switch (47) are separated as the hinged door (43) is opened, the circuit with the safety relay (57) is not completed and the Mechanical Mixer is stopped.

It is preferable to have a programmable relay (63), start button (65), stop button (67) located outside of the enclosed device. The programmable relay (63) may be connected to power supply (55) via a terminal strip (69), bus or other similar device. The programmable relay (63) allows for setting of time of operation, modification of angle of movement, speed of movement and the like. The start button (65) and stop button (67) are likewise located outside of the enclosed device, preferably located adjacent to the hinged door (43). If the programmable relay (63) is utilized, the desired settings can be imputed for each sample and the start button (65) and stop button (67) can control the operation of the Mechanical Mixer (31).

Foam Specific Volume

Foam specific volume is measure by placing a container of a known volume or marked with known volumes onto a mass balance, tarring the mass of the container and then dispensing from a foaming dispenser into the container. Record the resulting volume and the resulting mass of the foam. Dividing the volume by the mass of the foam results in the foam specific volume having the units of ml/g.

Formulations

Developer Composition Formulations

TABLE 1

Developer Composition 1

| Ingredient | Wt % (by weight Developer) | A Wt % (by weight Developer) |
|---|---|---|
| Hydrogen peroxide (50% active) | 10-15 | 12.3 |
| Phosphoric acid | 0.005 | 0.005 |
| Water | To 100 | To 100 |

TABLE 2

Developer Composition 2

| Ingredient | Wt % (by weight of developer) | B Wt % (by weight of developer) |
|---|---|---|
| Etidronic acid | 0.02 | 0.02 |
| Hydrogen peroxide (50% active) | 1-20 | 18.3 |
| Water | To 100 | To 100 |

TABLE 3

Tint Compositions

| INCI Ingredient Name | Black shades Wt % (by weight of tint) | Black shades C Wt % (by weight of tint) | red/auburn shades Wt % (by weight of tint) | red/auburn shades D Wt % (by weight of tint) | light shades (blond shades) Wt % (by weight of tint) | light shades (blond shades) E Wt % (by weight of tint) |
|---|---|---|---|---|---|---|
| Ethoxydiglycol | 10-20 | 14.0 | 10-20 | 14.0 | 10-20 | 14.0 |
| Propylene Glycol | 1-5 | 4.0 | 1-5 | 4.0 | 1-5 | 4.0 |
| Isopropyl Alcohol | 1-10 | 5.0 | 1-10 | 5.0 | 1-10 | 5.0 |
| Soytrimonium Chloride | 1-10 | 7.3 | 1-10 | 7.3 | 1-10 | 7.3 |
| Oleth-5 | 1-10 | 3.0 | 1-10 | 3.0 | 1-10 | 3.0 |
| Oleic Acid | 1-10 | 3.25 | 1-10 | 3.75 | 1-10 | 3.75 |
| Oleth-2 | 0.5-5 | 1.5 | 0.5-5 | 1.5 | 0.1-5 | 1.5 |
| Ammonium hydroxide | 1-10 | 4.1 | 5-15 | 7.8 | 1-15 | 8.5 |
| Fragrance or Parfum | 0.5-5 | 1.2 | 0.5-5 | 1.2 | 0.1-5 | 1.2 |
| Cocamidopropyl Betaine | 5-15 | 6.8 | 1-15 | 6.8 | 1-10 | 6.8 |
| Trisodium Ethylenediamine Disuccinate | 1-15 | 6.7 | 1-10 | 6.7 | 1-10 | 6.7 |
| C11-15 Pareth-9 | 0.5-5 | 1.25 | 0.5-5 | 1.25 | 0.1-5 | 1.25 |
| C12-15 PARETH -3 | 0.05-3 | 0.5 | 0.1-2 | 0.5 | 0.05-1 | 0.5 |
| Citric Acid | 0.05-3 | 0.4 | 0.1-2 | 0.4000 | 0.05-1 | 0.4 |
| Erythorbic Acid | 0.05-3 | 0.4 | 0.1-2 | 0.4000 | 0.05-1 | 0.4 |
| Sodium Sulfite | 0.05-3 | 0.1 | 0.05-1 | 0.1000 | 0.01-1 | 0.1 |
| EDTA | 0.01-1 | 0.05 | 0.01-1 | 0.0500 | 0.01-1 | 0.05 |
| P-Phenylenediamine | 0.5-5 | 1.98 | 0.05-1 | 0.15 | 0.01-1 | 0.08 |
| Resorcinol | 0.05-3 | 0.9 | 0.05-1 | 0.2 | 0.01-1 | 0.04 |
| Phenyl methyl pyrazolone | 0.05-3 | 0.1 | 0.05-1 | 0.1000 | 0.01-1 | 0.07 |
| M-Aminophenol | 0.5-5 | 1.3 | — | — | 0.005-0.1 | 0.013 |
| P-Aminophenol | — | — | 0.1-2 | 0.66 | 0.005-0.1 | 0.015 |
| 1-Naphthol | — | — | 0.01-1 | 0.0640 | 0.005-0.1 | 0.0260 |
| N,N-Bis(2-Hydroxyethyl)-P-Phenylenediamine Sulfate | 0.5-5 | 1.2 | 0.005-0.1 | 0.015 | — | — |

TABLE 3-continued

Tint Compositions

| INCI Ingredient Name | Black shades B Wt % (by weight of tint) | Black shades C Wt % (by weight of tint) | red/auburn shades Wt % (by weight of tint) | red/auburn shades D Wt % (by weight of tint) | light shades (blond shades) Wt % (by weight of tint) | light shades (blond shades) E Wt % (by weight of tint) |
|---|---|---|---|---|---|---|
| 4-Amino-2-hydroxytoluene | — | — | 0.1-2 | 0.47 | — | — |
| 2-Methylresorcinol | — | — | — | — | 0.05-1 | 0.1970 |
| Water | To 100% | To 100% | To 100% | To 100% | To 100% | To 100% |

TABLE 4

Tint Compositions

| Ingredient | F Natural Light Neutral Blonde % by wt | G Light Blonde % by wt | H Medium Gold Brown % by wt | I Rich Black % by wt | J Intense Red Violet Blonde % by wt |
|---|---|---|---|---|---|
| propylene glycol | 7 | 7 | 7 | 7 | 7 |
| ethoxydiglycol | 14 | 14 | 14 | 14 | 14 |
| Perfume | 0.75 | 0.75 | 0.75 | 0.75 | 0.75 |
| trisodium ethylenediamine disuccinate | 3.35 | 3.35 | 3.35 | 3.35 | 3.35 |
| citric acid | 0.4 | 0.4 | 0.4 | — | 0.4 |
| isopropyl alcohol | 5.0 | 5.0 | 5.0 | 5.0 | 5.0 |
| ammonium hydroxide (30%) | 8.25 | 8.0 | 7.5 | 5.0 | 5.0 |
| sodium sulfite | 0.1 | 0.1 | 0.1 | 0.1 | 0.1 |
| EDTA | 0.05 | 0.05 | 0.05 | 0.05 | 0.05 |
| Sodium Chloride | 1.9 | 1.8 | 1.4 | 0.3 | 0.8 |
| erythorbic acid | 0.4 | 0.4 | 0.4 | 0.4 | 0.4 |
| m-aminophenol (dye) | 0.013 | 0.007 | 0.009 | 0.6 | — |
| 1-naphthol (dye) | 0.026 | — | 0.0642 | — | — |
| toluene-2,5-diamine sulphate (dye) | 0.21 | 0.46 | 1.536 | 3.84 | 0.35 |
| n,n-bis(2-hydroxyethyl)-p-phenylenediamine sulphate (dye) | — | — | 0.0212 | — | — |
| resorcinol (dye) | 0.044 | — | 0.082 | 1.1 | — |
| p-aminophenol (dye) | 0.015 | — | 0.223 | — | — |
| 2-methylresorcinol (dye) | 0.197 | — | 0.385 | — | — |
| 4-amino-2-hydroxytoluene (dye) | — | — | 0.0093 | — | 1.76 |
| 1-hydroxyethyl 4,5-diamino pyrazole sulphate (dye) | — | — | — | 0.08 | 2.5 |
| phenyl methyl pryazolone (dye) | 0.05 | — | 0.1 | 0.1 | 0.1 |
| 2,4-Diaminophenoxyethanol HCl | — | — | — | 0.7 | — |
| 5-EthylOAP | — | — | 0.0132 | — | — |
| 2-amino-6-chloro-4-nitrophenol | — | 0.01 | — | — | — |
| water | to 100% | to 100% | to 100% | to 100% | to 100% |

TABLE 5

Developer Composition

| Ingredient | K % by weight of developer composition | L % by weight of developer composition | M % by weight of developer composition | N % by weight of developer composition | O % by weight of developer composition | P % by weight of developer composition |
|---|---|---|---|---|---|---|
| EDTA disodium dihydrate | 0.04 | 0.04 | 0.04 | 0.04 | 0.04 | 0.04 |
| Etidronic acid | 0.08 | 0.08 | 0.08 | 0.08 | 0.08 | 0.08 |
| Hydrogen peroxide (50% active) | 18.45 | 18.45 | 18.45 | 18.45 | 18.45 | 18.45 |
| ACULYN® 33 | 10.5 | 8.0 | 7.0 | 5.5 | 2.0 | 3.0 |
| ACULYN® 22 | 2.92 | 5.5 | 6.5 | 8.0 | 10.0 | 6.5 |
| water | to 100% | to 100% | to 100% | to 100% | to 100% | to 100% |

TABLE 6

| Tint | Developer | Tint/Developer Ratio (by weight ratio) | Foamer Choice | Foam Specific Volume (ml/g) | Average Dispensed (g/stroke) | Amount Dispensed (ml/stroke) | Low shear viscosity (cps) |
|---|---|---|---|---|---|---|---|
| Table 3; formulation C | Table 1; Formulation A | 62:62 | Squeeze foamer* | 9.2 | 1.3 | 12.0 | 100,000 |
| Table 3; formulation D | Table 2; Formulation B | 62:62 | Squeeze foamer* | 9.6 | 1.3 | 12.5 | 130,000 |
| Table 3; formulation E | Table 2; Formulation B | 62:62 | Squeeze foamer* | 9.0 | 1.4 | 12.7 | 70,000 |

*The squeeze foamer is selected to have a structure similar to that shown in FIG. 1 with the following dimensions selected:
1. air ingress orifice size: 0.4-0.6 mm diameter of circular orifice
2. liquid ingress orifice total area: 3.14 mm$^2$
3. liquid ingress orifice number of orifices: 3
4. mesh system in fluid connection after mixing chamber egress: 2 contiguous meshes with 170 μm openings.
5. mesh in fluid connection before dispensing orifice: 1 mesh 70 μm opening
6. mixing chamber egress orifice size: 1 mm diameter of circular orifice
7. dip-tube diameter: 3 mm

TABLE 7

| Tint | Developer | Tint/Developer Ratio (by weight ratio) | Foamer Choice | Foam Specific Volume (ml/g) | Average Dispensed (g/stroke) | Amount Dispensed (ml/stroke) |
|---|---|---|---|---|---|---|
| Table 4; formula G | Table 5; formula P | 1:1 | Squeeze foamer* | 35.31 | 3.3 | 10.7 |
| Table 3; formula E | Table 2; formula B | 1:1 | Squeeze foamer* | 20.90 | 2.2 | 9.5 |

*The squeeze foamer is selected to have a structure similar to that shown in FIG. 3 with the following dimensions selected:
air ingress orifice size: 0.7 mm diameter
liquid ingress orifice total area: 1.87-2.45 mm$^2$
liquid ingress orifice number of orifices: 3
mesh system in fluid connection after mixing chamber egress: 1 mesh with 170 μm openings.
mesh in fluid connection before dispensing orifice: 1 mesh with 170 μm opening
mixing chamber egress orifice size: 1 mm diameter of a circular orifice
dip-tube diameter: 3 mm The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A personal care article comprising:
(1) a personal care composition comprising a low-shear viscosity of at least 100 cps; the personal care composition being shear-thinning;
(2) a manually-actuable, non-aerosol dispensers comprising:
(a) a reservoir for holding a liquid to be dispensed in the form of foam; the reservoir comprises a volume such that the reservoir volume is larger than the volume of the personal care composition contained within the reservoir; the reservoir further comprising a headspace, the headspace comprising air;
(b) a foamer assembly which can be mounted on or in an opening of the reservoir; the foamer assembly comprises a dip tube, a mixing chamber and a dispensing head; the dip tube extends into the reservoir and into contact with the personal care composition, the dip tube fluidly connecting the mixing chamber with the personal care composition, the mixing chamber fluidly connected to a dispensing head, the dispensing head comprising a foam fluid connection contained within the dispensing head and the dispensing head further comprising a dispensing orifice; the foam fluid connection containing one or more porous elements wherein the one or more porous elements comprises three meshes, wherein two meshes are contiguous with each other in close proximity to the mixing chamber egress orifice and wherein one mesh is located in close proximity to the foamer dispensing orifice;

the mixing chamber comprises an outer wall which defines an internal volume of the mixing chamber; the outer wall comprises a top edge comprising a circumference; the circumference defining a top area; the mixing chamber further comprising at least one air ingress orifice, at least one liquid ingress orifice and at least one mixing chamber egress orifice having an area of between about 0.314 mm$^2$ to about 9.42 mm$^2$;

wherein the at least one air ingress orifice and at least one liquid ingress orifice are selected such that a ratio of personal care composition to air is from about 1:6 to about 1:15; and wherein the dispensor dispenses a foamed personal care composition comprising a foam specific volume from about 6 mL/g to about 14 mL/g.

2. The personal care article of claim 1, wherein the manually-actuable, non-aerosol dispenser has a foam output per stroke from about 0.5 gram/stroke to about 5.0 gram/stroke.

3. The personal care article of claim 1, wherein the manually-actuable, non-aerosol dispenser has a foam output per stroke from about 3 mL/stroke to about 70 mL/stoke.

4. The personal care article of claim 1 wherein the at least one air ingress orifice and at least one liquid ingress orifice are orientated so that the personal care composition is mixed with air.

5. The personal care article of claim 1, wherein the mixing chamber further comprising a diffuser plate, the diffuser plate comprising the mixing chamber egress.

6. The personal care article of claim 5, wherein the mixing chamber egress has an area of between about mm$^2$ 2.512 mm$^2$ to about 5.652 mm$^2$.

7. The personal care article of claim 1, wherein the air of the headspace enters into the mixing chamber by the air ingress orifice; the headspace is in direct communication pathway to the mixing chamber through the air ingress orifice.

8. The personal care article of claim 1, wherein the personal care composition is fluidly communicated from the reservoir by the dip tube to the mixing chamber by an indirect communication with the mixing chamber.

9. The personal care article of claim 8, wherein the personal care composition is conveyed from the reservoir, through the dip tube into a void volume external to the mixing chamber.

10. The personal care article of claim 1, wherein the dip tube comprises a diameter of greater than 2.0 mm.

11. The personal care article of claim 1, wherein the foamer assembly further comprises a ball valve, silicone seal or gasket located in communication with the headspace of the reservoir.

12. The personal care article of claim 1, wherein the two meshes in close proximity to the mixing chamber egress orifice comprise about 170 micron (μ) opening size and wherein the one mesh located in close proximity to the foamer dispensing orifice comprises about a 70 micron (μ) opening size.

13. The personal care article of claim 1, wherein the mixing chamber egress orifice comprises an area of 3.14 mm$^2$.

14. The personal care article of claim 13, wherein the mixing chamber egress orifice is provided in the diffuser plate.

15. The personal care article of claim 1, wherein the mixing chamber egress orifice comprises a diameter of 1.75 mm, the first mesh has a mesh opening size of about 170 micron (μ), and the mesh comprises a mesh opening size of about 70 micron (μ).

16. The personal care article of claim 1, wherein the personal care composition is a hair colorant composition.

17. The personal care article of claim 1, wherein the personal care composition is a body wash composition.

18. The personal care article of claim 1, wherein the personal care composition is a facial wash composition.

19. The personal care article of claim 1, wherein the personal care composition is a shampoo composition.

20. A personal care article comprising:
(1) a personal care composition comprising a low-shear viscosity of at least 100 cps; the personal care composition being shear-thinning;
(2) a manually-actuable, non-aerosol dispensers comprising:
(a) a reservoir for holding a liquid to be dispensed in the form of foam; the reservoir comprises a volume such that the reservoir volume is larger than the volume of the personal care composition contained within the reservoir; the reservoir further comprising a headspace, the headspace comprising air;
(b) a foamer assembly which can be mounted on or in an opening of the reservoir;

the foamer assembly comprises a dip tube, a mixing chamber and a dispensing head; the dip tube extends into the reservoir and into contact with the personal care composition, the dip tube fluidly connecting the mixing chamber with the personal care composition, the mixing chamber fluidly connected to a dispensing head, the dispensing head comprising a foam fluid connection contained within the dispensing head and the dispensing head further comprising a dispensing orifice; the foam fluid connection containing one or more porous elements wherein the one or more porous elements comprises three meshes, wherein two meshes are contiguous with each other in close proximity to the mixing chamber egress orifice and wherein one mesh is located in close proximity to the foamer dispensing orifice;

the mixing chamber comprises an outer wall which defines an internal volume of the mixing chamber; the outer wall comprises a top edge comprising a circumference; the circumference defining a top area; the mixing chamber further comprising at least one air ingress orifice, at least one liquid ingress orifice and at least one mixing chamber egress orifice having an area of between about 0.314 mm$^2$ to about 9.42 mm$^2$;

wherein the mixing chamber egress orifice area is selected to be smaller than the top area of the mixing chamber; and wherein the dispensor dispenses a foamed personal care composition comprising a foam specific volume from about 6 mL/g to about 14 mL/g.

21. A personal care article comprising:
(1) a personal care composition comprising a low-shear viscosity of at least 100 cps; the personal care composition being shear-thinning;
(2) a manually-actuable, non-aerosol dispensers comprising:
(a) a reservoir for holding a liquid to be dispensed in the form of foam; the reservoir comprises a volume such that the reservoir volume is larger than the volume of the personal care composition contained within the reservoir; the reservoir further comprising a headspace, the headspace comprising air;
(b) a foamer assembly which can be mounted on or in an opening of the reservoir; the foamer assembly comprises a dip tube, a mixing chamber and a dispensing head; the dip tube extends into the reservoir and into contact with the personal care composition, the dip tube fluidly connecting the mixing chamber with the personal care composition, the mixing chamber fluidly connected to a dispensing head, the dispensing head comprising a foam fluid connection contained within the dispensing head and the dispensing head further comprising a dispensing orifice; the foam fluid connection containing one or more porous elements wherein the one or more porous elements comprises three meshes, wherein two meshes are contiguous with each other in close proximity to the mixing chamber egress orifice and wherein one mesh is located in close proximity to the foamer dispensing orifice;

the mixing chamber comprises an outer wall which defines an internal volume of the mixing chamber; the outer wall comprises a top edge comprising a circumference; the circumference defining a top area; the mixing chamber further comprising at least one air ingress orifice, at least one liquid ingress orifice and at least one mixing chamber egress orifice having an area of between about 0.314 mm$^2$ to about 9.42 mm$^2$;

wherein the at least one air ingress orifice and at least one liquid ingress orifice are selected such that the manually-actuable, non-aerosol dispensers has a foam output from about 3 mL/stroke to about 70 mL/stoke with a foam specific volume of about 6 mL/g to about 14 mL/g.

\* \* \* \* \*